United States Patent
Wing et al.

(10) Patent No.: US 7,931,623 B2
(45) Date of Patent: Apr. 26, 2011

(54) TROCAR SYSTEM

(75) Inventors: Daniel M. Wing, Utica, NY (US);
Deborah A. Laun, Syracuse, NY (US);
Frank J. Witkowski, Syracuse, NY (US)

(73) Assignee: ConMed Corporation, Utica, NY (US)

( * ) Notice: Subject to any disclaimer, the term of this patent is extended or adjusted under 35 U.S.C. 154(b) by 302 days.

(21) Appl. No.: 12/029,018

(22) Filed: Feb. 11, 2008

(65) Prior Publication Data

US 2008/0132847 A1    Jun. 5, 2008

Related U.S. Application Data

(60) Division of application No. 10/264,530, filed on Oct. 4, 2002, now Pat. No. 7,344,519, which is a continuation-in-part of application No. 09/944,190, filed on Aug. 31, 2001, now Pat. No. 6,989,003.

(51) Int. Cl.
*A61M 5/178* (2006.01)
(52) U.S. Cl. .................................................. 604/167.05
(58) Field of Classification Search .............. 604/167.05
See application file for complete search history.

(56) References Cited

U.S. PATENT DOCUMENTS

| | | | |
|---|---|---|---|
| 4,424,833 A | 1/1984 | Spector et al. | 137/849 |
| 4,601,710 A | 7/1986 | Moll | 604/165 |
| 4,909,798 A | 3/1990 | Fleischhacker et al. | 604/256 |
| 5,104,383 A | 4/1992 | Shichman | 604/167 |
| 5,129,885 A | 7/1992 | Green et al. | 604/164 |
| 5,152,754 A | 10/1992 | Plyley et al. | 604/164 |
| 5,154,701 A | 10/1992 | Cheer et al. | 604/167 |
| 5,197,955 A | 3/1993 | Stephens et al. | 604/167 |
| 5,203,769 A | 4/1993 | Clement et al. | 604/32 |
| 5,209,736 A | 5/1993 | Stephens et al. | 604/164 |
| 5,224,929 A | 7/1993 | Remiszewski | 604/30 |
| 5,261,891 A | 11/1993 | Brinkerhoff et al. | 604/165 |
| 5,263,937 A | 11/1993 | Shipp | 604/164 |
| 5,342,316 A | 8/1994 | Wallace | 604/167 |
| 5,346,459 A | 9/1994 | Allen | 606/185 |
| 5,357,974 A | 10/1994 | Baldridge | 128/754 |
| 5,364,372 A | 11/1994 | Danks et al. | 604/264 |
| 5,368,046 A | 11/1994 | Scarfone et al. | 128/754 |
| 5,380,288 A | 1/1995 | Hart et al. | 604/167 |
| 5,385,553 A | 1/1995 | Hart et al. | 604/167 |
| D358,209 S | 5/1995 | Petruschke et al. | D24/146 |

(Continued)

FOREIGN PATENT DOCUMENTS

EP    0 480 653    4/1992

(Continued)

OTHER PUBLICATIONS

The DetachaPort™ System, Resposable Trocars, Imagyn Surgical Brochure, 4 pages, 1997.

(Continued)

*Primary Examiner* — Nicholas D Lucchesi
*Assistant Examiner* — Jason Flick

(57) ABSTRACT

A trocar system includes a cannula having a cannula head and a cannula tube, and an obturator having a cap and either a rounded tip or a cutting blade. The head and cap form an ergonomically shaped bulbous handle. At least a portion of an outer surface of the cannula head may include a resilient non-slip material. The cannula head may also include a monolithic housing having a port with a Luer Lock fitting and an integrally formed passageway for receiving a stopcock valve.

25 Claims, 17 Drawing Sheets

U.S. PATENT DOCUMENTS

| | | | |
|---|---|---|---|
| 5,549,565 A * | 8/1996 | Ryan et al. | 604/167.03 |
| 5,556,411 A | 9/1996 | Taoda et al. | 606/185 |
| 5,603,702 A | 2/1997 | Smith et al. | 604/256 |
| 5,634,908 A | 6/1997 | Loomas | 604/167 |
| 5,643,301 A | 7/1997 | Mollenauer | 606/167 |
| 5,669,875 A | 9/1997 | Van Eerdenburg | 604/22 |
| 5,720,759 A | 2/1998 | Green et al. | 606/167 |
| 5,752,938 A | 5/1998 | Flatland et al. | 604/167 |
| 5,758,655 A | 6/1998 | Como Rodriguez et al. | 128/749 |
| 5,800,451 A | 9/1998 | Buess et al. | 606/185 |
| 5,807,338 A | 9/1998 | Smith et al. | 604/164 |
| 5,820,600 A | 10/1998 | Carlson et al. | 604/167 |
| 5,824,002 A | 10/1998 | Gentelia et al. | 604/164 |
| 5,827,228 A | 10/1998 | Rowe | 604/167 |
| 5,857,982 A | 1/1999 | Milliman et al. | 600/567 |
| 5,865,807 A | 2/1999 | Blake, III | 604/167 |
| 5,865,812 A | 2/1999 | Correia | 604/248 |
| 5,868,714 A | 2/1999 | Danks | 604/256 |
| 5,879,332 A | 3/1999 | Schwemberger et al. | 604/164 |
| 5,897,503 A * | 4/1999 | Lyon et al. | 600/459 |
| 5,904,699 A | 5/1999 | Schwemberger et al. | 606/185 |
| 5,941,852 A | 8/1999 | Dunlap et al. | 604/165 |
| 5,976,121 A | 11/1999 | Matern et al. | 606/1 |
| 5,989,224 A | 11/1999 | Exline et al. | 604/167 |
| 5,989,228 A | 11/1999 | Danks et al. | 604/256 |
| 5,993,471 A | 11/1999 | Riza et al. | 606/185 |
| 6,017,356 A | 1/2000 | Frederick et al. | 606/185 |
| 6,036,711 A | 3/2000 | Mozdzierz et al. | 606/185 |
| 6,063,099 A | 5/2000 | Danks et al. | 606/185 |
| 6,123,689 A | 9/2000 | To et al. | 604/256 |
| 6,159,182 A * | 12/2000 | Davis et al. | 604/167.06 |
| 6,228,061 B1 | 5/2001 | Flatland et al. | 604/167.06 |
| 6,258,065 B1 | 7/2001 | Dennis et al. | 604/167.03 |
| 6,482,181 B1 | 11/2002 | Racenet et al. | 604/167.06 |
| 6,497,687 B1 | 12/2002 | Bianco | 604/274 |
| 6,500,188 B2 | 12/2002 | Harper et al. | 606/169 |
| 6,551,282 B1 | 4/2003 | Exline et al. | 604/167.01 |
| 6,569,119 B1 | 5/2003 | Haberland et al. | 604/167.03 |
| 6,595,946 B1 | 7/2003 | Pasqualucci | 604/27 |
| D495,053 S | 8/2004 | Laun | D24/146 |
| D495,054 S | 8/2004 | Laun et al. | D24/146 |
| 6,989,003 B2 | 1/2006 | Wing et al. | 604/161 |
| D533,275 S | 12/2006 | Laun | D24/146 |
| D559,387 S | 1/2008 | Witkowski et al. | D24/146 |
| 7,344,519 B2 | 3/2008 | Wing et al. | 604/167.03 |
| 2002/0013552 A1 | 1/2002 | Dennis | 604/167.03 |
| 2002/0072713 A1 | 6/2002 | Almond et al. | 604/167.05 |
| 2002/0103420 A1 | 8/2002 | Coleman et al. | 600/173 |
| 2003/0040711 A1 | 2/2003 | Racenet et al. | 604/167.06 |
| 2004/0260244 A1 | 12/2004 | Piechowicz et al. | 604/167.06 |

FOREIGN PATENT DOCUMENTS

| | | |
|---|---|---|
| EP | 536549 A1 | 4/1993 |
| EP | 0 792 660 A2 | 2/1997 |
| WO | WO 00/45720 | 8/2000 |
| WO | WO 02/30305 | 4/2002 |
| WO | WO 02/41795 | 5/2002 |

OTHER PUBLICATIONS

ConMed Brochure entitled, "Advanced Patent Benefits, Single Use Trocars," dated 2000.

ConMed Brochure entitled, "TroGard Finesse," dated Feb. 2000.

* cited by examiner

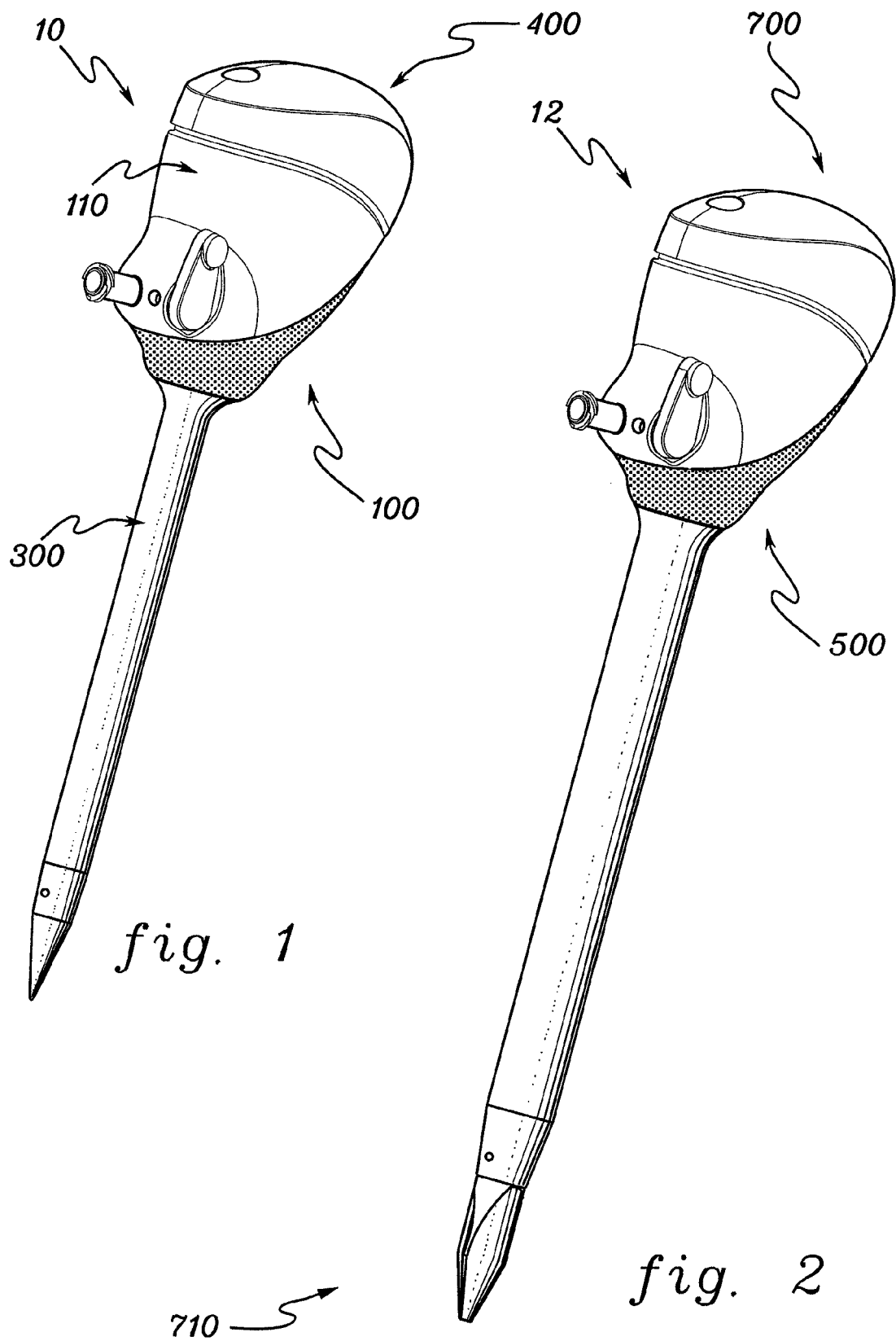

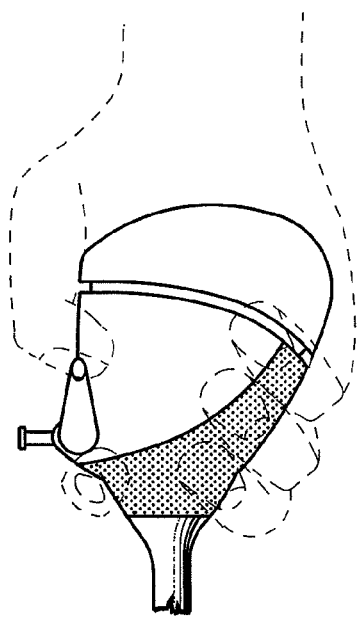
fig. 5
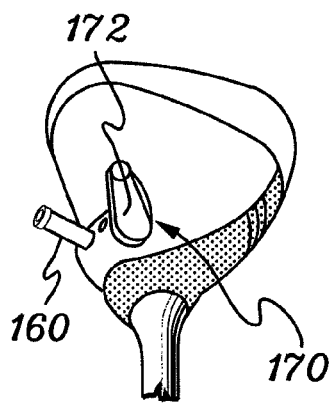 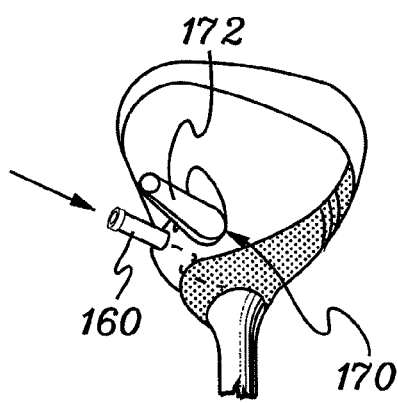 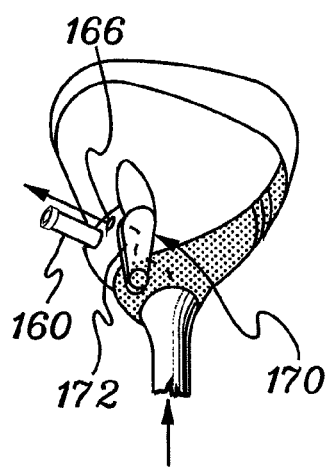
fig. 6  fig. 7  fig. 8

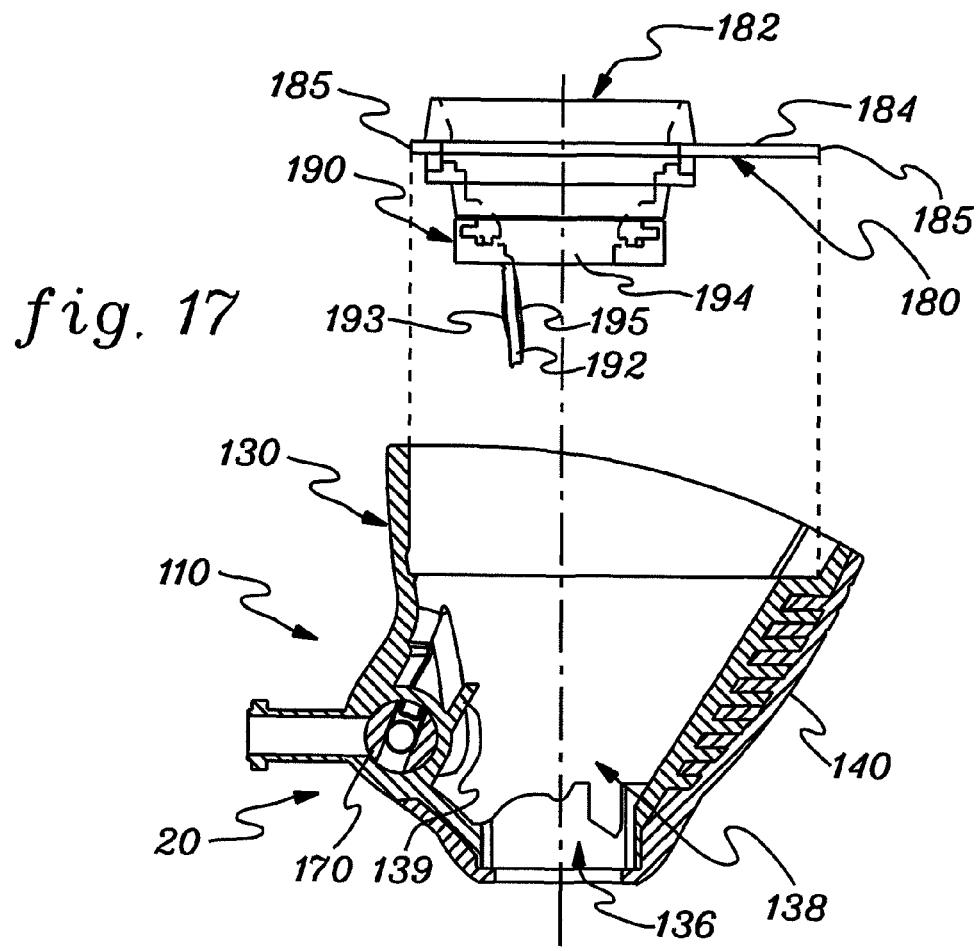
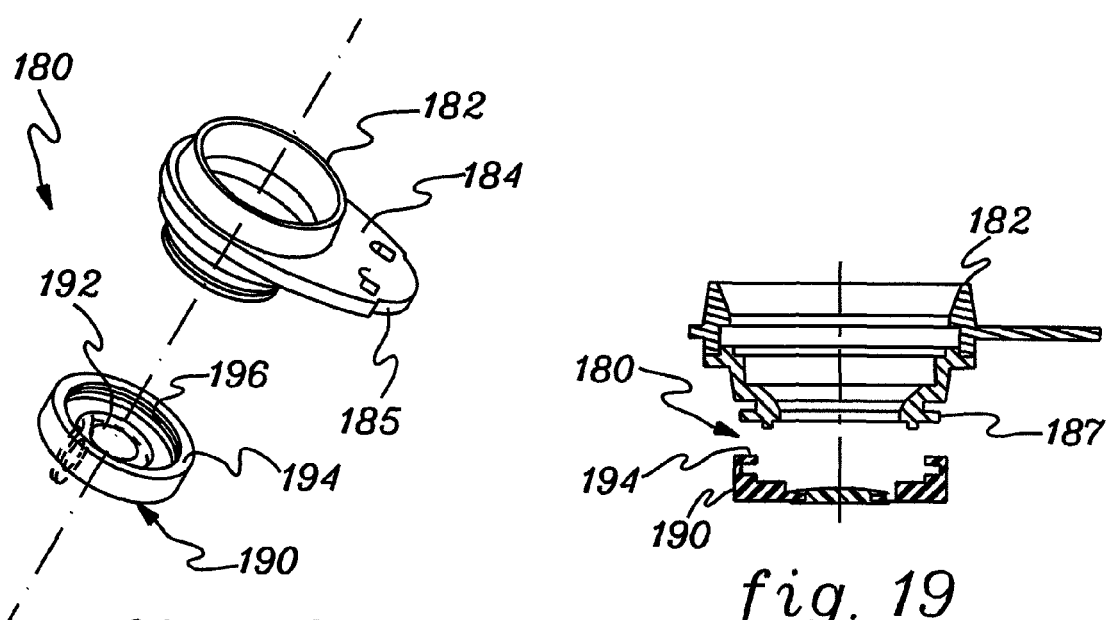

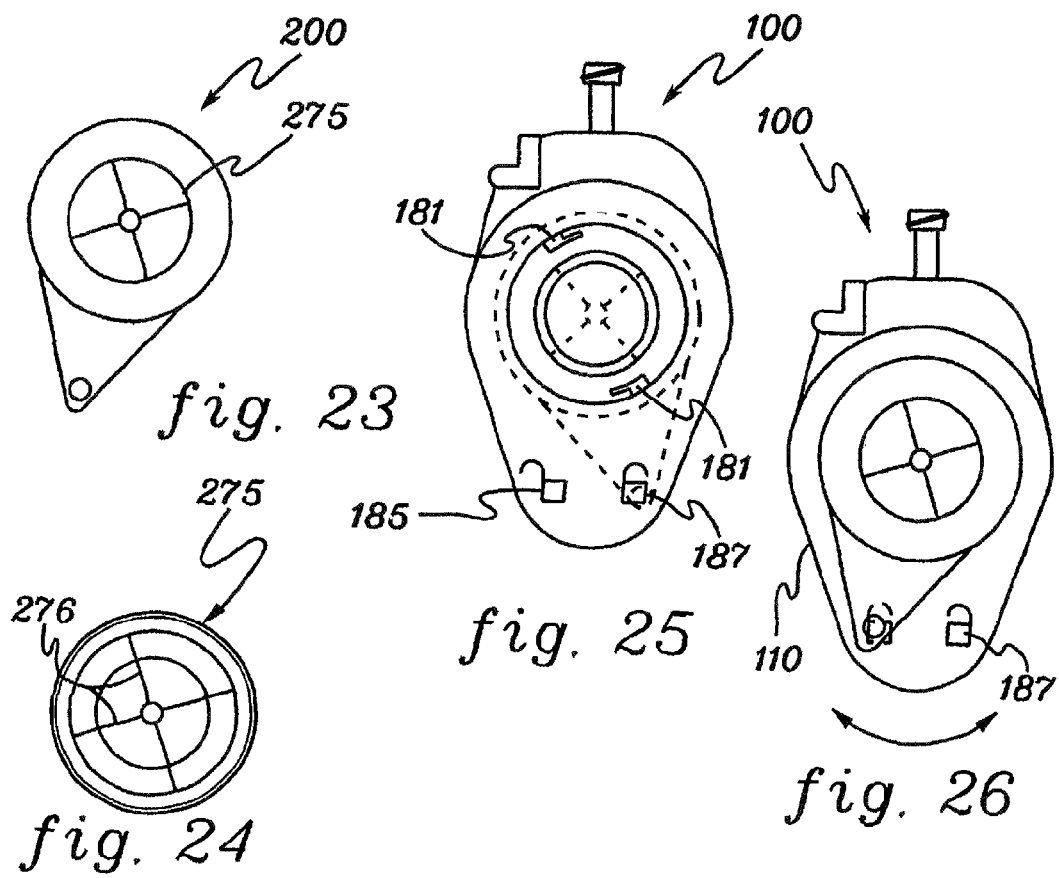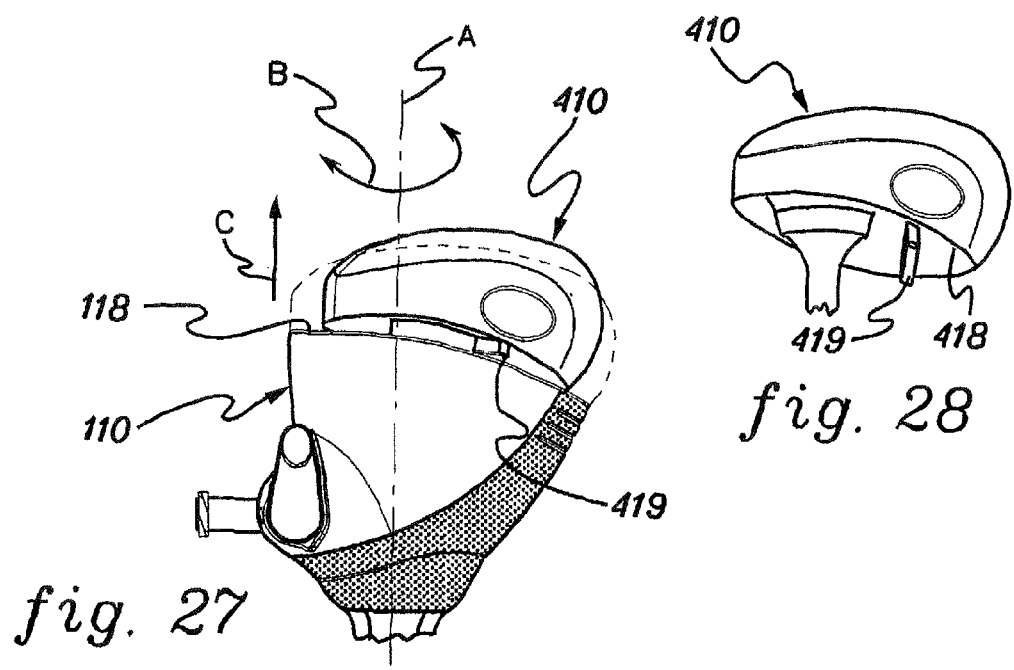

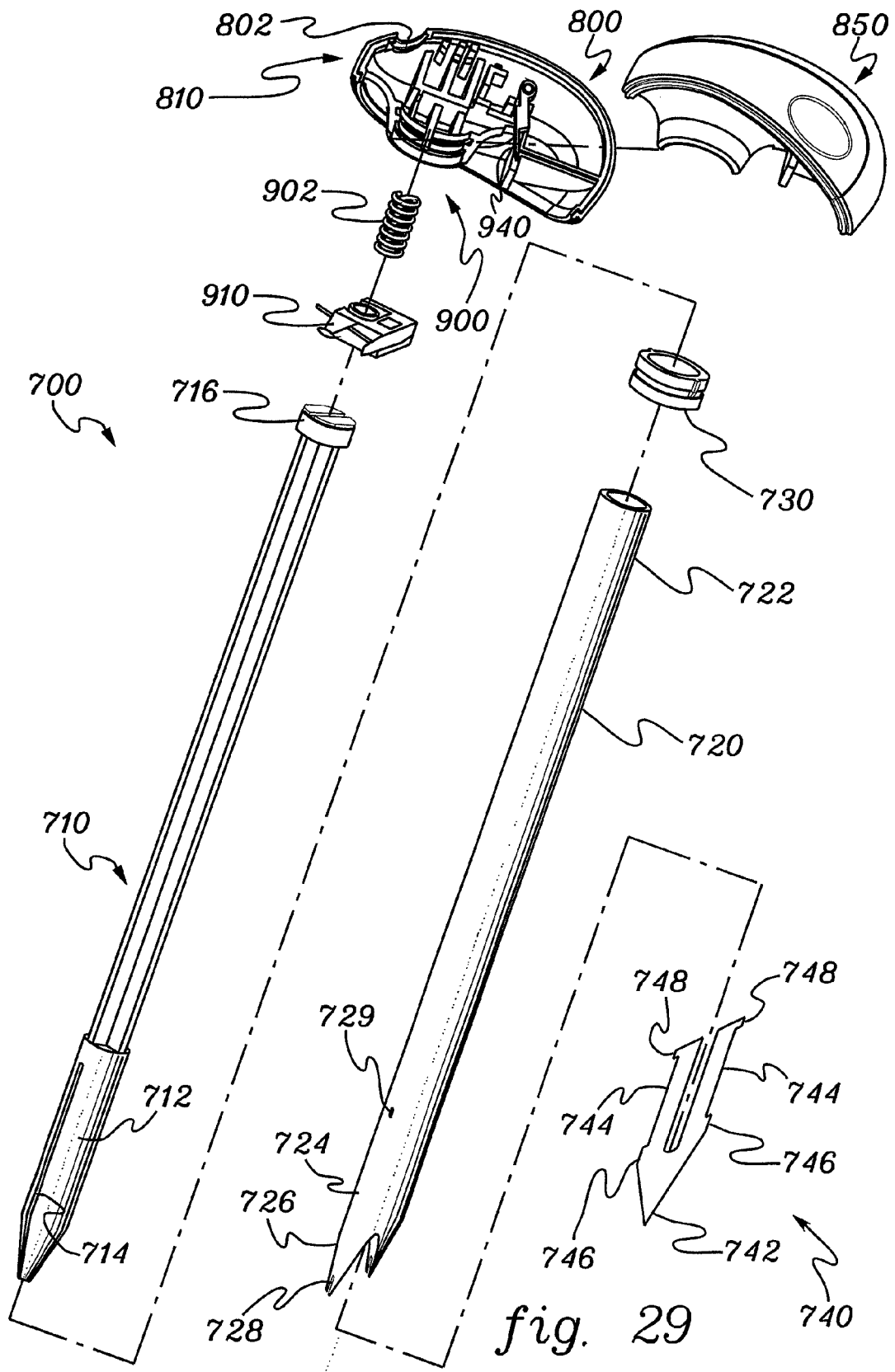

TROCAR SYSTEM

CROSS-REFERENCE TO RELATED APPLICATION

This application is a divisional of U.S. patent application Ser. No. 10/264,530, filed Oct. 4, 2002 and entitled "Trocar System," which is a continuation-in-part of U.S. patent application Ser. No. 09/944,190, filed Aug. 31, 2001 and entitled "Obturator and Cannula For A Trocar Adapted For Ease Of Insertion And Removal," and which issued as U.S. Pat. No. 6,989,003, the entire subject matter of which is these applications are incorporated herein by reference.

TECHNICAL FIELD

This invention relates generally to surgical instruments, and more particularly to trocar systems for providing an opening through tissue and into body cavities and through which surgical instruments may be inserted.

BACKGROUND OF THE INVENTION

Trocar systems are surgical devices used to obtain access to a body cavity to perform various surgical procedures such as laparoscopic surgery or arthroscopic surgery.

A trocar system typically includes a pointed rod-like device or obturator fitted into a tube-like device or cannula. A pointed end of the obturator projects out an end of a cannula tube and is used to penetrate the outer tissue of the cavity. After the tissue is penetrated and the body cavity is accessed by the trocar system, the obturator is then withdrawn while the cannula tube is retained in the cavity. The body cavity can then be accessed by surgical instruments via the cannula tube to perform various surgical procedures, or the cannula can simply be used as a drainage outlet.

There is a need for improved trocar systems which allow a surgeon to provide an opening in a cavity of a patient and though which surgical instruments may be inserted.

SUMMARY OF THE INVENTION

In one aspect, the present invention provides a cannula head for use in a trocar system having an obturator. The cannula head includes a housing having a first passageway extending therethrough for receiving the obturator. The housing also includes a distal opening and a proximal opening to the first passageway, and at least a portion of an outer surface of the housing comprises a resilient non-slip material.

In another aspect, the present invention provides a cannula head for use in a trocar system having an obturator. The cannula head also includes a housing having a first passageway extending therethrough for receiving the obturator. The housing also includes a distal opening and a proximal opening to the first passageway. A port having a Luer Lock fitting is connectable in fluid communication with the first passageway, and the housing and the port with the Luer lock fitting are monolithic.

In another aspect, the present invention provides a cannula head for use in a trocar system having an obturator. The cannula head includes a housing having a first passageway extending therethrough for receiving the obturator. The housing also includes a distal opening and a proximal opening to the first passageway. An outer surface of the housing includes a reduced distal portion, an enlarged proximal portion, an enlarged front portion, and a reduced rear portion.

In another aspect, the present invention provides a cannula head for use in a trocar system having an obturator. The cannula head includes a housing having a first passageway extending therethrough for receiving the obturator. The housing also includes a distal opening and a proximal opening to the first passageway. A port having a Luer Lock fitting is connectable in fluid communication with the first passageway, and the housing and the port with the Luer lock fitting are monolithic. A stopcock valve having a lever is installed in the housing for regulating the flow of fluid through the port. At least a portion of an outer surface of the housing includes a resilient non-slip material. A flapper valve is disposed across the passageway within the housing, and a releasably attachable seal is connectable to the housing across the proximal opening. The outer surface of the housing includes a reduced distal portion, an enlarged proximal portion, an enlarged front portion, and a reduced rear portion.

In another aspect, the present invention provides a cannula for use in a trocar system having an obturator. The cannula includes a cannula head and a reusable and releasably attachable cannula tube defining a passageway extending therethrough. The cannula head includes a housing having a resilient material for forming a seal between the housing and the cannula tube.

In further aspects, the present invention also provides trocar systems which include the above-mentioned cannula heads along with a cannula tube and an obturator.

In another aspect, the present invention provides an ergonomically shaped trocar system which includes a cannula having a proximal head and an obturator having a proximal cap. The obturator is insertable into the cannula so that its cap is adjacent the head. The head and the cap are shaped so that when the obturator is inserted into the cannula with the head end cap in alignment, the head and the cap together form a bulbous, substantially continuous outer surface grippable by a human hand. At least a portion of the head comprises a non-slip material.

In another aspect, the present invention provides an ergonomically shaped trocar system which includes a cannula having a proximal head and an obturator having a proximal cap. The head and the cap are shaped so that when the obturator is inserted into the cannula with the head and cap in alignment, the head and the cap together comprise a handle having a reduced distal portion, an enlarged proximal portion, an enlarged forward portion, and a reduced rear portion.

In another aspect, the present invention provides a method for forming a cannula head of a trocar system in which the method includes forming a housing comprising a rigid material and attaching a non-slip material to the housing.

In another aspect, the present invention provides a method for forming a monolithic cannula head for use with a trocar system having an obturator. The method includes integrally forming a housing having a port having a Luer Lock fitting. The housing includes a first passageway extending therethrough for receiving the obturator and the housing includes a distal opening and a proximal opening to the first passageway, and the port is connectable in fluid communication with the first passageway.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed descriptions of the various embodiments and the accompanying drawings in which:

FIG. 1 is a perspective view of a dilating trocar system in accordance with the present invention;

FIG. 2 is a perspective view of a cutting trocar system in accordance with the present invention;

FIG. 5 is a right side elevational view of the trocar systems of FIGS. 1 and 2, grasped by a hand illustrated in dashed lines;

FIGS. 6-8 are perspective views of the trocar system of FIG. 1 with a stopcock valve disposed in the various operating positions;

FIG. 17 is a cross-sectional view of the cannula head of FIG. 1 showing a lower seal with a flapper valve open;

FIG. 18 is an exploded perspective view of the lower seal of FIG. 17;

FIG. 19 is an exploded cross-sectional view of the lower seal of FIG. 17;

FIG. 23 is a top view of the releasably attachable upper seal of FIG. 20;

FIG. 24 is a top view of a protective covering guide of the releasably attachable upper seal of FIG. 23;

FIG. 25 is a top view of the cannula head of FIG. 20 with the releasably attachable upper seal shown in dashed lines in an unlocked position;

FIG. 26 is a top view of the cannula head of FIG. 20 with the releasably attachable upper seal shown in a locked position;

FIG. 27 is a right side elevational view of the trocar system of FIG. 1 with the obturator rotated relative to the cannula;

FIG. 28 is a perspective view of the obturator of FIG. 27;

FIG. 29 is an exploded perspective view of the obturator of FIG. 2;

DETAILED DESCRIPTION OF THE INVENTION

Figure 3:
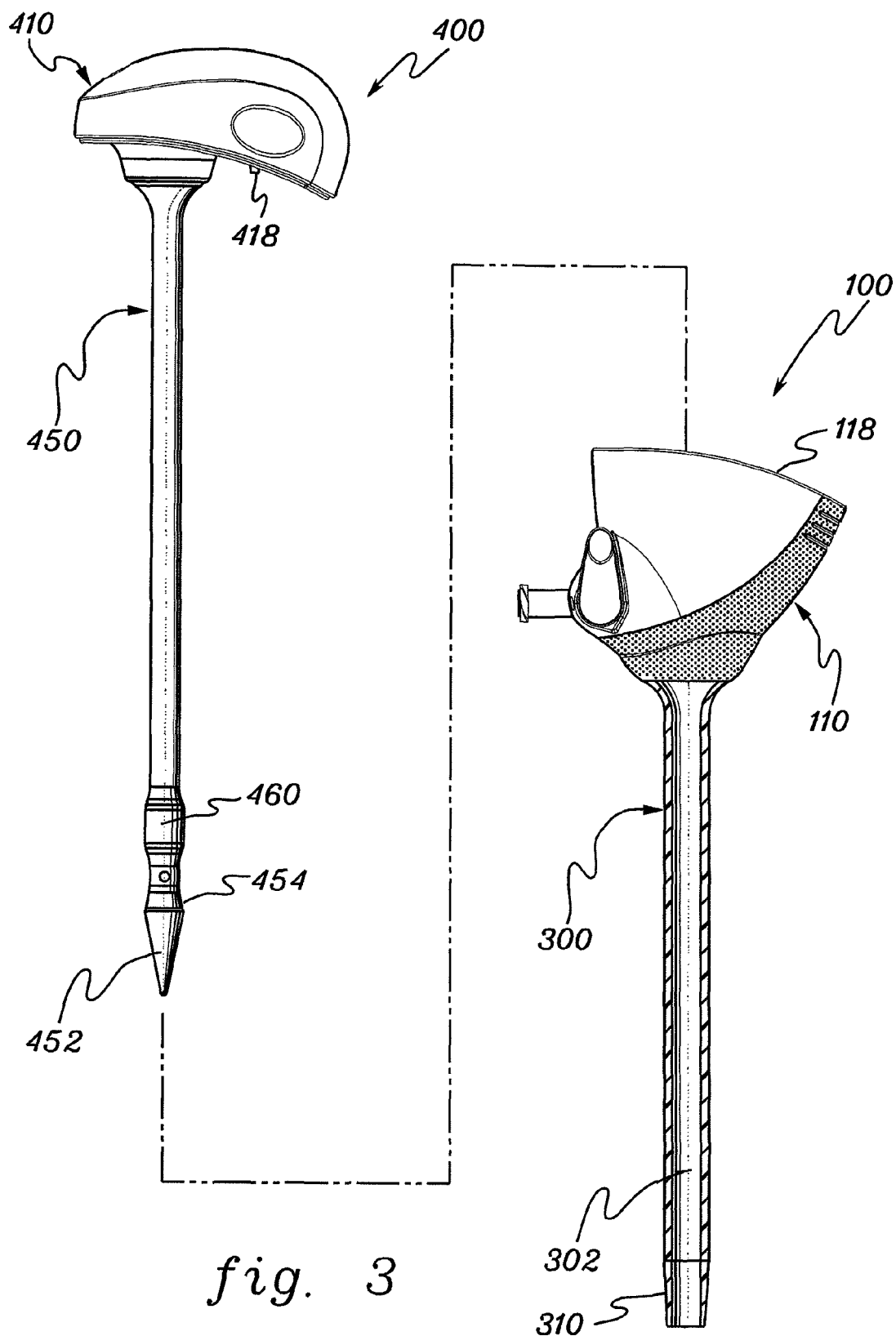
FIG. 3 is a right side elevational view, in part cross-section, of the dilating trocar system of FIG. 1 showing the obturator removed from the cannula.
Figure 4:
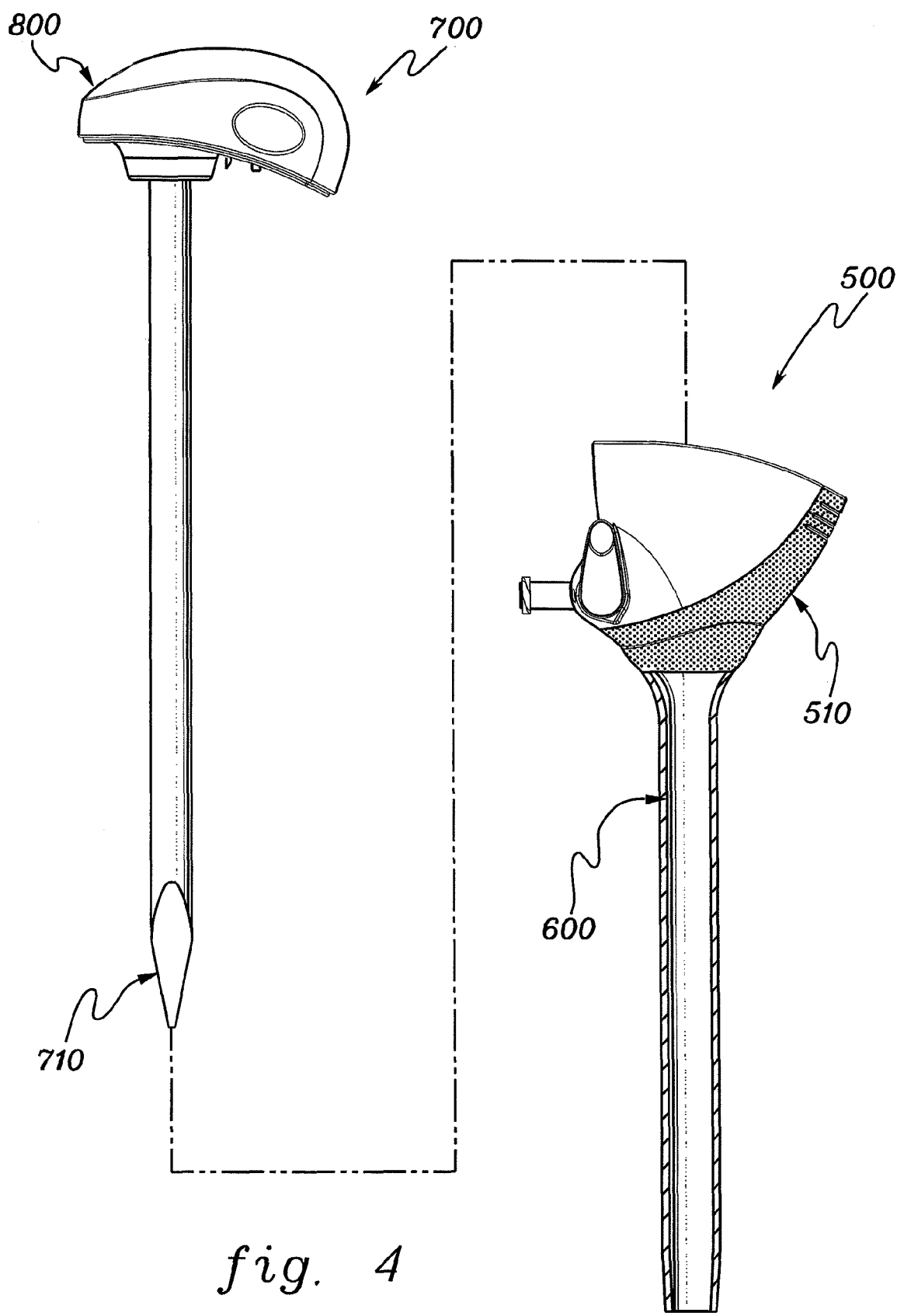
FIG. 4 is a right side elevational view, in part cross-section, of the cutting trocar system of FIG. 2 showing the obturator removed from the cannula.

FIGS. 1 and 2 illustrate perspective views of a dilating trocar system 10 and a safety-shielded cutting trocar system 12, respectively, in accordance with the present invention. With reference to FIGS. 1 and 3, trocar system 10 generally includes a cannula 100 having a cannula head 110 and a cannula tube 300 into which is slidably receivable a dilating obturator 400 having an obturator cap 410 attached to an elongated shaft 450 having a pointed end 452 which may have a rounded point at its distal end. With reference to FIGS. 2 and 4, trocar system 12 generally includes a cannula 500 having a cannula head 510 and a cannula tube 600 into which is slidably receivable a safety shielded cutting obturator 700 having a spring-loaded shield 710 and automatically-operated spring-loaded locking mechanism for inhibiting the exposure of a cutting blade (not shown in FIG. 4) after passing through tissue or muscle, as described in greater detail below. The cutting trocar system cuts or lacerates tissue when obtaining access to a body cavity. The dilating trocar systems allow parting and stretching of, for example, multiple cross-directional muscle layers and intra-abdominal blood vessels, when gaining access to a body cavity.

With reference to FIG. 5, one aspect of the present invention includes the trocar system having an ergonomically-shaped handle (when the obturator is inserted in the cannula with the cap and head in alignment) which may be described as having a bulbous configuration, an egg-shaped or ovoid configuration, or a modified pistol grip which readily conforms to and may be easily grasped by a surgeon in one hand. The handle is designed to accommodate the cannula tube between the index and middle finger when holding the trocar system. The ring finger and pinky are able to wrap around the lower narrow portions of the handle. The rearmost portion of the obturator may also be curved to conform to a surgeon's hand and to allow the surgeon to apply pressure when inserting the trocar system into a patient. Another aspect of the present invention includes the handle having an resilient non-slip material which allows a surgeon to better grip the cannula head and thereby reduce the likelihood of surgeon's hand slipping relative to the handle.

In operation, the pointed end of the trocar system is used to penetrate the outer tissue of a cavity. After the tissue is penetrated and the body cavity is accessed by the trocar system, the obturator is then withdrawn from the cavity while the cannula tube is retained in the cavity. The body cavity can then be accessed by surgical instruments via the cannula tube to perform various surgical procedures, or the cannula can simply be used as a drainage outlet.

In addition, in another aspect of the present invention, the trocar system may include a port and a stopcock for permitting the introduction and venting of a pressurized fluid through the cannula tube for insufflating a body cavity when providing a pneumoperitoneum. For example, with reference to FIGS. 6-8, a stopcock valve 170 may be operated by hand, for example, by a surgeon, to one of three positions during use. As described in greater detail below, in a first position with a handle 172 of stopcock valve 170 in an upward position, as shown in FIG. 6, fluid is inhibited from entering or exiting the cannula. In a second position, with handle 172 of stopcock valve 170 in an outward position as shown in FIG. 7, a pressurized fluid is permitted to flow into the cannula via a port 160 and through the inside of the cannula tube. In a third position, with handle 172 of stopcock valve 170 in a downward position, as shown in FIG. 8, pressurized fluid is permitted to vent out of the cannula via an opening 166.

As also explained in greater detail below, another aspect of the present invention includes the various components forming the trocar systems comprising interchangeable parts or assemblies which may also be releasably attachable, thereby reducing the number of different components that need to be manufactured and the cost associated therewith in forming the various trocar systems.

Figure 10:
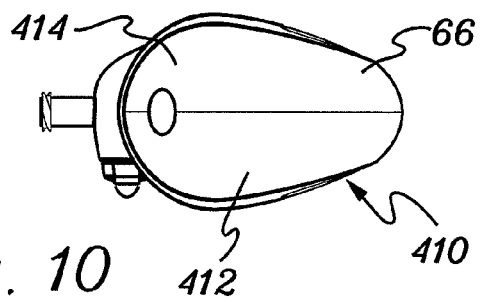
FIG. 10 is a top view of the combination cannula head and obturator cap of FIG. 9.
Figures 9, 12, 13:
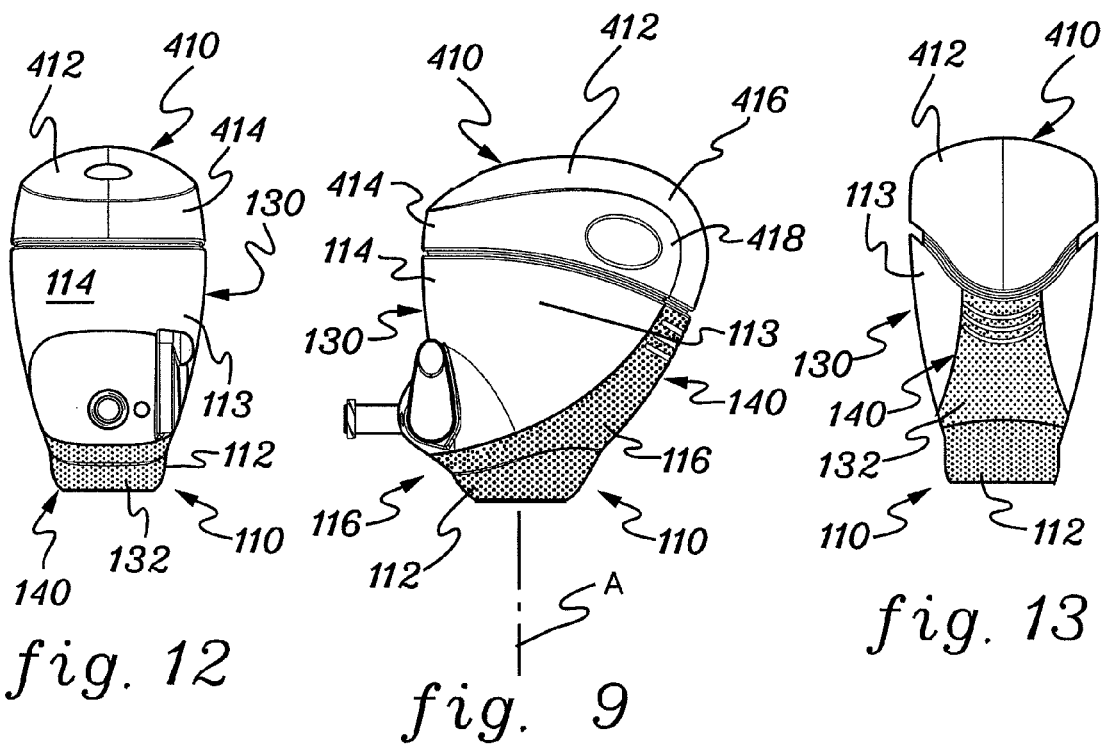
FIG. 9 is a right side elevational view of the combination cannula head and obturator cap of the trocar system of FIG. 1.
FIG. 12 is a front view of the combination cannula head and obturator cap of FIG. 9.
FIG. 13 is a rear view of the combination cannula head and obturator cap of FIG. 9.
Figure 11:
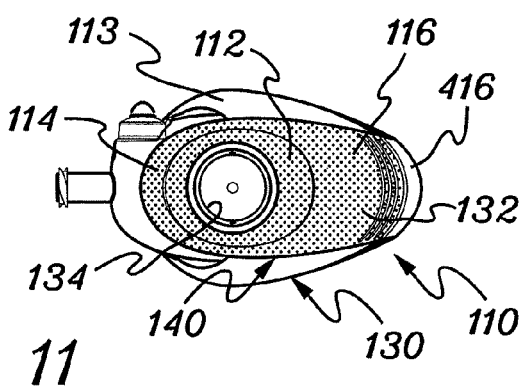
FIG. 11 is a bottom view of the combination cannula head and obturator cap of FIG. 9.

With reference again to FIG. 1, and as best shown in FIGS. 9-13, an outer surface of the combination of cannula head 110 and obturator cap 410 may include, for example, a reduced distal portion 112, an enlarged proximal portion 113 and 412, enlarged front portions 114 and 414, and reduced rear portions 116 and 416. A longitudinal axis A (FIG. 9) of the trocar system may extend through the reduced distal portion 112 and the enlarged front portions 114 and 414 of the combination of the cannula head and obturator cap so that the handle is asymmetrically disposed relative to axis A. When viewed along axis A, for example, as shown in FIGS. 10 and 11, the combination of the cannula head and obturator may have a modified oval-shaped cross-section. In particular, it may be seen that the forward portion of the cross section is larger in girth than the rearward portion.

Cannula head 110 may also comprise a generally rigid cannula housing 130 and a resilient non-slip material 140. Resilient non-slip material 140 may extend along a rear of the cannula housing, and/or around a distal opening 134 (FIG. 6) of cannula housing 130. The resilient non-ship material allows a surgeon to better grip the trocar system compared to a cannula head being formed solely from a rigid material having a smooth outer surface.

Figure 14:
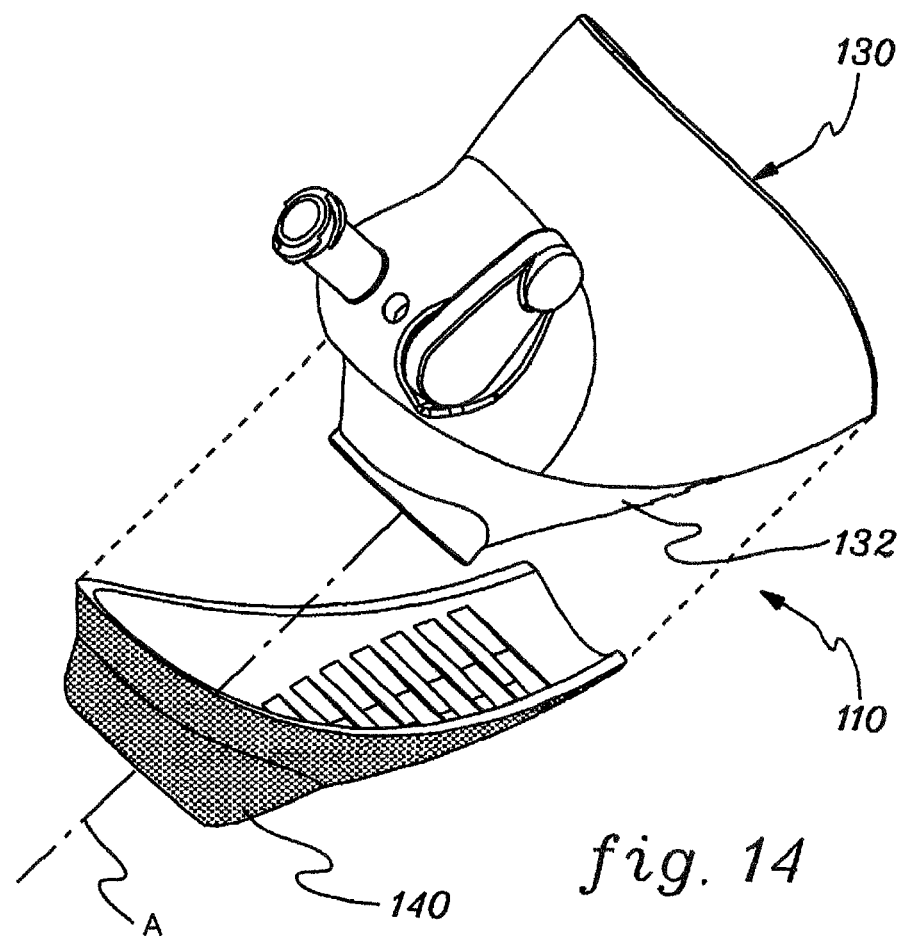
FIG. 14 is an exploded perspective view of the rigid cannula housing and the resilient non-slip material of the cannula head of FIG. 1.

With reference to FIG. 14, the outer surface of cannula housing 130 may have a recessed portion 132 for receiving resilient non-slip material 140 either as a separately formed piece attached with an adhesive, or a piece formed by an injection overmolding process onto cannula housing 130. The cannula housing may be formed of a rigid plastic material such as ABS (acrylonitrile-butadiene-styrene), polycarbonate, or polystyrene. The resilient non-slip material may be a resilient or an elastomeric material, for example, silicone rubber, polyurethane elastomer, neoprene or thermo plastic elastomer.

Figure 15:
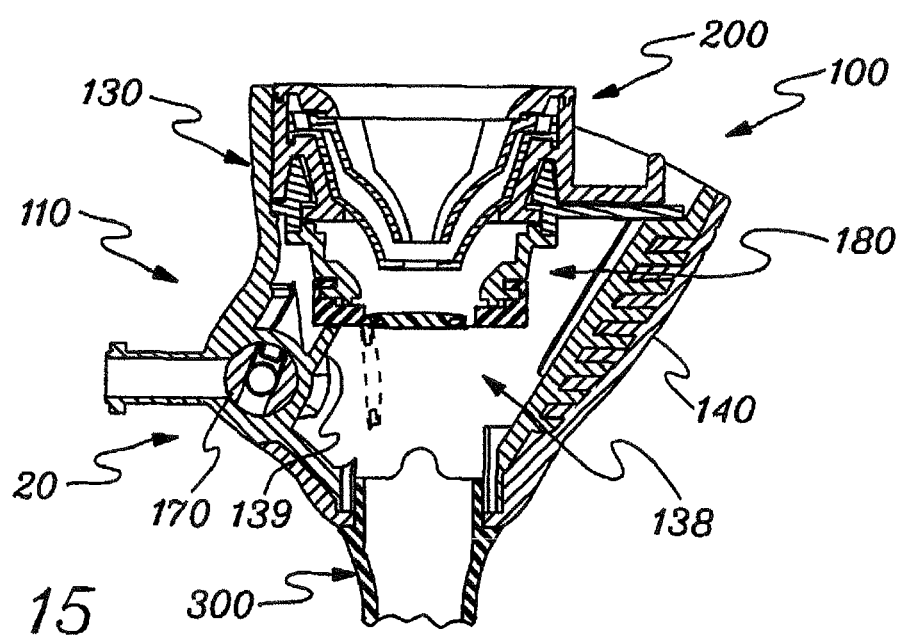
FIG. 15 is enlarged cross-sectional view of the cannula of FIG. 1.

As shown in FIG. 15, cannula 100 includes cannula head 110 and cannula tube 300. Cannula head 110 may comprise cannula housing 130, resilient non-slip material 140, a releasably attachable stopcock valve 170, a lower seal 180, and a releasably attachable upper seal 200.

Figure 16:
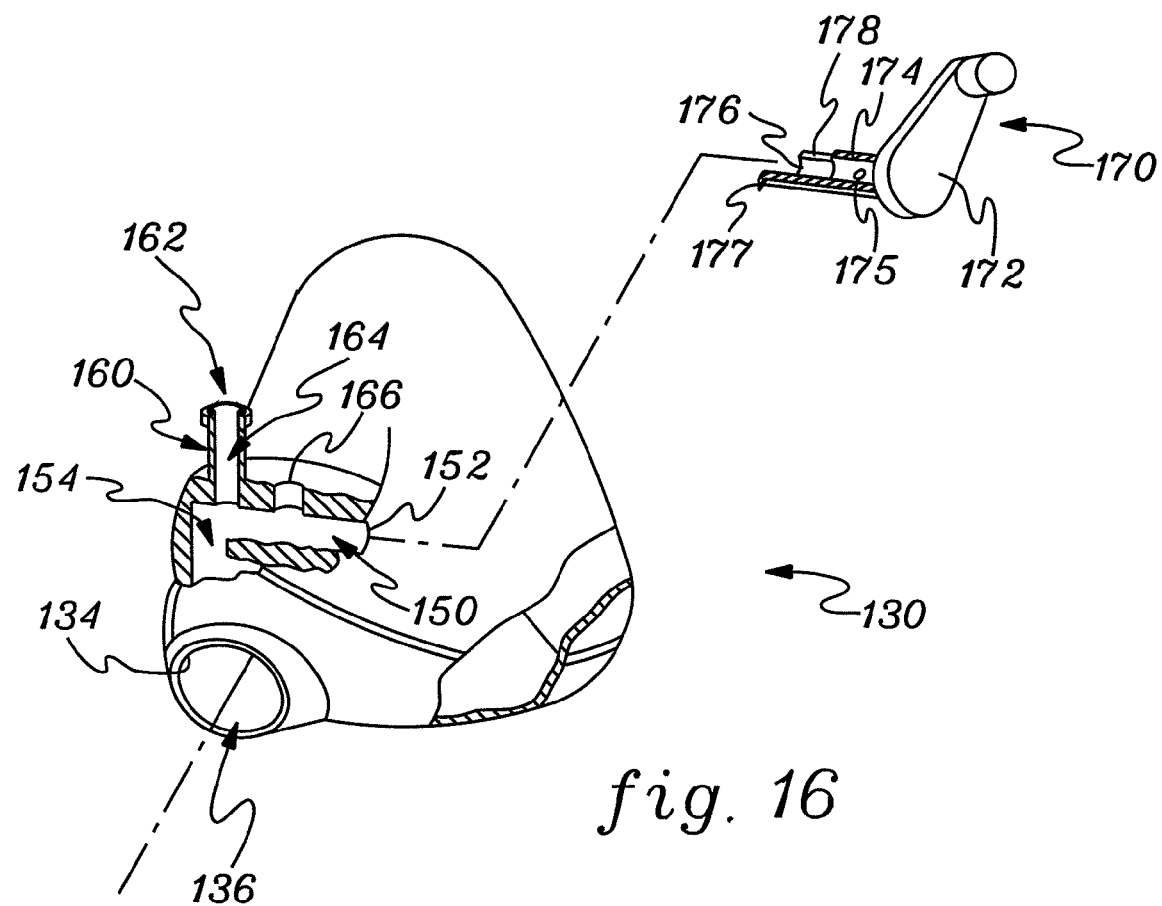
FIG. 16 is a perspective view of the cannula housing, in part cross-section and partially cutaway, and the stopcock valve of FIG. 1.

With reference to FIG. 16, another aspect of the present invention includes cannula housing 130 comprising a monolithic or one-piece housing. Cannula housing 130 may include a first passageway 136 having distal opening 134, and a plurality of passageways for receiving the stopcock valve and for permitting the introduction and venting of a pressurized fluid through the cannula tube for insufflating a body cavity when providing a pneumoperitoneum. For example, a second passageway 150, in which is receivable stopcock valve 170, defines an outer opening 152 and an inner opening 154 opening into first passageway 136. Disposed on the front of monolithic cannula housing 130 is an integrally formed gas supply port 160 having integrally formed Luer lock 162, e.g., female Luer lock fitting. Port 160 comprises a third passageway 164 which opens into second passageway 150. Disposed adjacent to port 160 is aperture 166 which opens into second passageway 150. Desirably, the various configurations of the monolithic cannula housing, e.g., the passageways and port having integrally formed Luer lock fitting, reduce the need for assembling and sealing separately attachable pieces. The monolithic cannula housing may be formed by injection molding in a one step operation.

Stopcock valve 170 includes lever 172, a tubular member 174 comprising a passageway 176 therein and having a slot 178 (only half of which is shown in FIG. 16) at the end of the tubular member, and an aperture 175 extending through tubular member 174. A downwardly-depending detent 177 may be provided to engage the cannula housing forming opening 152 in a snap-fit manner to attach stopcock 170 to cannula housing 130 in second passageway 150.

With reference to FIGS. 17-19, lower seal 180 includes an outer support 182 and a flapper valve 190. Lower seal 180 is sealably attached across passageway 136 in cannula housing 130 behind stopcock valve 170 (best shown in FIG. 15). For example, an outer edge 185 of a lateral flange 184 may be attached with an adhesive (or other suitable means for forming a complete seal) along a support or ledge 131 formed in cannula housing 130 to define a chamber 138 in housing 130. Flapper valve 190 includes a flexible disc-shaped portion 192 (shown in an open position in FIG. 17) attached at a portion along its circumference to a flexible collar 194 having a groove 196 (FIG. 18) therein. A pair of rigid discs 193 and 195 (best shown in FIG. 17) may be attached to the center of flexible disc-shaped portion 192. The rigid discs may add support to and protect the flexible disc-shaped portion when an obturator or other instruments are inserted and removed from the cannula. Outer support 182 may be monolithic or integrally formed as one-piece. Outer support 182 may also include a circumferentially extending flange 187 (best shown in FIG. 19) on which is received flexible collar 194 of flapper valve 190. When no instrument is inserted in the cannula, the flapper valve 190 is normally closed, i.e., biased shut. In addition, if the cannula housing is pressurized with a fluid, the pressurized fluid will exert a pressure against the flapper valve to more securely retain the flapper valve in a sealed position and maintain the pressure in the cannula housing and in the body cavity. As shown in FIGS. 15 and 17, housing 130 may include an inwardly-extending tab 139 which abuts flapper valve 190 adjacent to where flexible disc-shaped portion 192 attaches to flexible collar 194 when lower valve 190 is attached to housing 130. In particular, tab 139 aids in retaining collar 194 or flapper valve 190 on outer support 182 when an obturator is inserted in the cannula.

Figure 20:
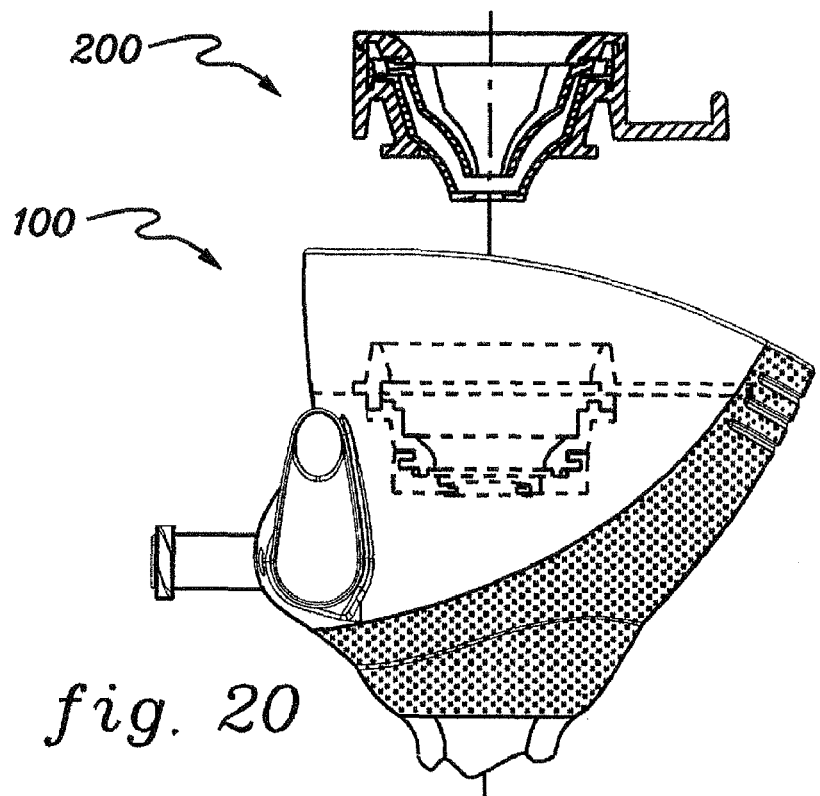
FIG. 20 is a right side elevational view of the cannula of FIG. 1 showing a releasably attachable upper seal.
Figures 21, 22:
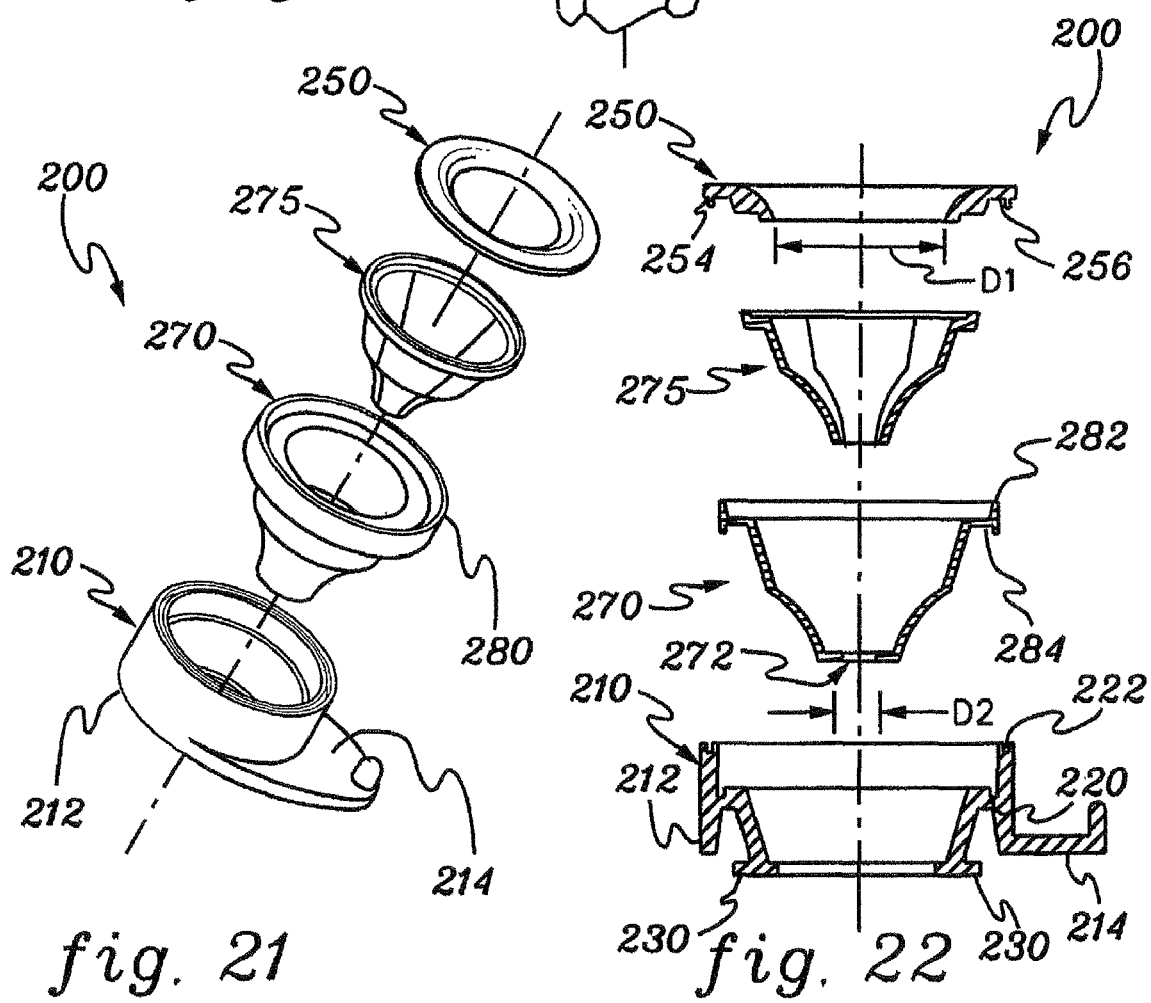
FIG. 21 is an exploded perspective view of the releasably attachable upper seal of FIG. 20.
FIG. 22 is an exploded cross-sectional view of the releasably attachable upper seal of FIG. 20.

Cannula 100 may also include a second releasably attachable upper seal 200. As best shown in FIGS. 20-22, second releasably attachable upper seal 200 includes a distal support 210, a proximal support 250, a protective guide 275, and a flexible seal 270. Distal support 210 includes a ring-shaped portion 212 and an outwardly-extending arm 214. As explained in greater detail below, outwardly extending arm 214 aids a surgeon in locking and unlocking upper seal 200 to cannula head 110. The distal and proximal supports may be made from a rigid plastic material, and the flexible seal may be made from a resilient or elastomeric material, for example, silicone rubber, polyurethane elastomer, neoprene or thermo plastic elastomer.

As shown in FIG. 22, flexible seal 270 includes a centrally located aperture or hole 272 which allows for the easy insertion and removal of, for example, an obturator shaft into the cannula while minimizing the release of fluid from the cannula. Flexible seal 270 may also include inwardly extending flanges which engage, for example, the shaft of an obturator. Desirably, the tip of the obturator forms a seal with the opening of the flexible seal prior to the tip of the obturator contacting flapper valve 190 of the lower seal.

Flexible seal 270 may include an upper seal portion 280 having an upwardly-extending annular flange 282 and a downwardly-depending annular flange 284 which is sandwiched between an upper edge of protective guide 275 and an annular groove 220 in distal support 210. An outer downwardly-depending flange 254 of proximal support 250 may be received in and attached to an annular groove 222 in distal support 220 with an adhesive. Proximal support 250 may also have a concave shape for directing the tip of an obturator or other instruments through upper seal 200.

FIG. 23 illustrates a top view of releasably attachable seal 200. The flexible seal may include protective guide 275 for protecting aperture or hole 272 in flexible seal 270 (FIG. 22) and guiding an obturator toward aperture or hole 272. The protective guide may be formed from a generally stronger material which is less susceptible to being punctured compared with the material forming seal 270 (FIG. 22). As shown in FIG. 24, the protective guide may also include a plurality of slits 276. Protective guide 275 may then be sandwiched between proximal support 250 and flexible seal 270 with an adhesive to form a conical protective guide having slits which allows the passage of various sized instruments.

FIG. 25 illustrates a top view of cannula 100 with releasable attachable seal 200 shown in dashed lines in an unlocked position. FIG. 26 illustrates cannula 100 in which releasably attachable seal 200 is releasably attached to cannula head 110 by rotating releasably attachable seal 200 clockwise. Cannula head 110 and releasably attachable seal 200 may be releasably attachable, for example, via a bayonet-type connector, with releasably attachable seal 200 having two flexible pins or tabs 230 (FIG. 22) which extend outwardly and engage J-shaped grooves 181 (FIG. 25) in lower seal 180 of cannula head 110. It will be appreciated that other means for releasably attaching the upper seal to the cannula head may be employed. Alternatively, the cannula head may have a fixedly attached upper seal. In addition, indicia 185 and 187 may be provided on lower seal 180 for indicating the locked and unlocked positions of upper seal 200. By providing a releasably attachable upper seal, a surgeon may remove the upper seal to provide a greater opening for removing, for example, tissue through the cannula tube and cannula head. The aperture of the upper seal may be sized so that the aperture or hole 272 is slightly smaller than an obturator shaft or surgical instrument to be used. This interference fit between the resilient diameter of the aperture and the shaft minimizes the passage of fluid from a cavity to the ambient environment during insertion and removal of an obturator or other instruments. When an obturator, for example, is removed from cannula 100 and from the aperture, flapper valve 190 provides a seal to the ambient environment.

It will be appreciated by those skilled in the art that the diameter of the opening proximal support 250, the thickness of flexible seal 270, and the diameter of aperture 272, may vary depending upon the size of the cannula head, the size of the obturator or other instruments to be used, and the difference in pressure across the flexible seal that needs to be sealed. For example, a diameter D1 (FIG. 22) of the opening of proximal support 250 may be between about 0.625 inches and about 0.875 inches; a diameter D2 (FIG. 22) of the aperture in flexible seal 270 may be about 0.0625 inches to about 0.1875 inches; and the thickness of flexible seal 270 may be between about 1 mm to about 3 mm; and the thickness of the protective guide may be about 0.010 inches to about 0.030 inches.

With reference to FIGS. 3, 27, and 28, cannula head 110 may also include a proximal ridge 118 (FIGS. 3 and 27) which cooperates with a corresponding distal ridge 418. In addition, a flat bearing surface 419 may extend across the distal portion of obturator cap 410. After inserting the assembled trocar system into a patient, a surgeon can hold cannula head 110 stationary with one hand and easily remove obturator cap 410 with the other hand. As best shown in FIG. 27, by rotating obturator cap 410 in either direction relative to axis A, as illustrated by the curved double-headed arrow B, a portion of flat bearing surface 419 impinges and slidably engages or "rides up" proximal ridge 118 so that obturator cap 410 moves axially away from cannula head 110 as indicated by arrow C. The flat bearing surface may also be raised relative to the distal curved surface of the cap assembly. In addition, the sides of the raised flat bearing surface may be rounded to allow the edge of the raised flat bearing surface to easily ride up on ridge 118, i.e., the proximal curved surface of the cannula head.

A rotation as small as about 5 degrees will result in movement of the obturator cap away from the cannula head; however, the obturator cap will typically be rotated at least about 15 degrees, and preferably at least about 90 degrees, to effect the desired separation. The outward thrust of the obturator cap relative to the cannula head, though slight, can provide sufficient force and displacement to aid in the disengagement of the tip of the obturator from the distal end of the cannula tube and from tissue into which the obturator is inserted. Thereafter, the cannula head can held stationary while the shaft of the obturator is withdrawn completely from the cannula.

Many other means such as bosses, projections, and recesses may be employed to effect the desired sliding engagement or camming action and axial deflection for initially removing the obturator from the cannula head. For example, additional bearing surfaces and configurations for providing an outward thrust when rotating obturator cap relative to the cannula head are disclosed in U.S. patent application Ser. No. 09/944,190, filed Aug. 31, 2001 and entitled "Obturator and Cannula For A Trocar Adapted For Ease Of Insertion And Removal," the entire subject matter of which is incorporated herein by reference. The rotation, though preferably performed manually by the surgeon, can also be automated and performed remotely, for example, by a computer-controlled servo-mechanism.

With reference again to FIG. 3, obturator 400 includes shaft 450 with tip 452 which conically tapers from a first diameter, typically a maximum diameter of the shaft, to a rounded point. Tip 452 is designed to permit relatively easy insertion of trocar system 10 through, for example, the muscle and fascia of a patient and into a body cavity with minimal force and minimal damage to the tissue penetrated and minimal damage to the internal tissues and organs.

The surface of tip 452 typically defines an angle of between about 5 degrees and about 30 degrees and is preferably between about 15 degrees and about 25 degrees with the axis of the obturator. Tip 452 also includes a proximal conically-tapered surface 454. The surface of tapered section 454 typically defines an angle of between 10 degrees and about 50 degrees and is preferably between about 20 degrees and about 25 degrees. Obturator 400 may also include a land section 460 having a first leading tapered surface and a second trailing tapered surface. Land section 460 helps to center shaft 450 within cannula tube 302 during insertion and removal of the obturator. Tapered surfaces of the land and tip also aid in facilitating the insertion and removal of the obturator through the seal(s) of the cannula head. The diameter of the land section is typically greater than the diameter of the shaft but less than maximum diameter of the tip. The land section typically has a length approximately equal to the diameter of the shaft.

Cannula tube 300 may be annular in cross-section with a relatively uniform inside diameter and outside diameter along the length of cannula tube 300. The inside diameter is typically greater than the outer diameter of the tip of the obturator to ensure that the obturator can be inserted without obstruction in cannula tube 300. Cannula tube 300 may include a distal end 310 that is uniformly continuous and thus has no interruptions, such as slots, holes, or other apertures. Such a uniform, continuous geometry minimizes the resistance to insertion through and removal from tissue, minimizes the potential for tissue to be torn or damaged during insertion and removal, and also minimizes the potential for damage to sutures, other instruments, and the trocar itself during insertion or removal.

In addition, the internal diameter and outside diameter of cannula tube 300 may decrease at end 310. The inside diameter and outside diameter of the cannula tube may taper to a minimum diameter at the distal most end of cannula tube 300. In accordance with another aspect of the present invention, the inside diameter of the end of cannula tube 300 may be smaller than the maximum diameter of the tip of the obturator.

Although the entire cannula tube can be made of flexible material, at least the distal end of the cannula tube is typically made of a flexible material, for example, a thermoplastic polymer, such as a polycarbonate or its equivalents, or a thermoset polymer, such as a polyurethane or its equivalents. Therefore, when the obturator is inserted into the cannula tube the tip of the obturator will approach the distal end of the cannula tube, the outer surface of the tip will contact and bear against the inside of the distal end of the cannula tube. The distal end of the cannula tube will then deflect radially. After the tip passes through the flexible distal end of the cannula tube, the flexible end recovers to essentially its undeflected size. The resulting assembled trocar system 10 provides a relatively uniform transition between the outer surface of the tip and the outside surface of the distal end of the cannula tube such that little or no resistance is provided and little or no damage occurs when subsequently inserting trocar system 10 through tissue. In addition, the obturator and cannula fit together in a snap-fit manner due to such a tip and distal end of the cannula tube. Such a configuration is further described in U.S. patent application Ser. No. 09/944,190, entitled "Obturator and Cannula for a Trocar Adapted for Ease of Insertion and Removal," filed Aug. 31, 2001, the entire subject matter of which is incorporated herein by reference.

Obturator 400 may be monolithic or comprise one-piece, for example, a metal material such as stainless steel, titanium, or aluminum, or a plastic material such as ABS (acrylonitrile-butadiene-styrene), polycarbonate, or polystyrene. Obturator 400 may also be comprised of two or more individual components or dissimilar materials. For example, the obturator cap, the shaft, and the tip may be formed from individual pieces and then assembled via threaded connections. In addition, obturator cap 410 may be made of plastic having a threaded connector with internal or external threads, and the shaft may be made of stainless steel with a threaded end which matingly engages the threaded connector of the obturator cap. The tip may also be an individual steel part which is threaded either internally or externally to the shaft.

With reference again to FIG. 2, safety shielded cutting obturator 700 may include both a spring-loaded shield and an automatic spring-loaded locking mechanism for inhibiting the exposure of the blade after passing through tissue or muscle. As explained in greater detail below, in a locked position, a safety shield 710 covers the cutting blade (not shown in FIG. 2) of the obturator. When in the unlocked position and when the trocar system is engaged for puncturing and pressure is applied against the body wall, the shield retracts to expose the cutting blade. After the body wall is punctured, the pressure is relieved and safety shield 710 springs back to cover the cutting blade and is locked in place. In this way, the likelihood of puncture of internal organs is reduced.

Safety shielded cutting obturator 700 is further shown in detail in FIG. 29. The obturator includes a two-piece obturator cap 800 which forms a portion of a grip or handle of trocar system 12 (FIG. 2) and in which is contained the locking mechanism. A hollow obturator tube 720 includes a proximal end 722 which is attached to a collar 730 which collar 730 is attached to obturator housing 800. A distal end 724 of obturator tube 720 includes a pair of tapered portions 726 each having at the distal end thereof a slot 728. A pair of slots 729 are also disposed along the obturator tube. A cutting blade 740 includes a cutting tip 742 and two spaced-apart longitudinally-extending legs 744 and 746 each having a pair of laterally-extending tabs 746 disposed adjacent tip 742, and a pair of laterally-extending tabs 748 disposed on the longitudinally-extending legs. Legs 744 are received in obturator tube 720 and orientated so that tabs 746 align with and fit into slots 728 and tabs 748 align with and fit into slots 729 to fixedly attach cutting blade 740 to obturator tube 720. The cutting blade and obturator tube may be formed from a metallic material.

Slidably receivable within obturator tube 720 is safety shield 710. Shield 710 includes an enlarged distal end 712 which is sized slightly smaller than the inside diameter of the obturator tube. Enlarged distal end 712 includes a slot 714 in which is receivable cutting blade 740. A proximal end 716 aligns with collar 730. As explained below, proximal end 716 may be locked in position so that enlarged distal end 712 covers cutting blade 740 and/or is biased to return enlarged distal end 712 to a covering position over cutting blade 740.

Proximal end 716 of shield 710 may be spring-loaded or distally biased by a biasing means such as a coiled spring 902 interposed between a releasably lockable plunger 910 and an inner wall of obturator cap 800. Releasably lockable plunger 910 may be automatically armed/disarmed upon actuation of an actuator 940.

Figure 30:
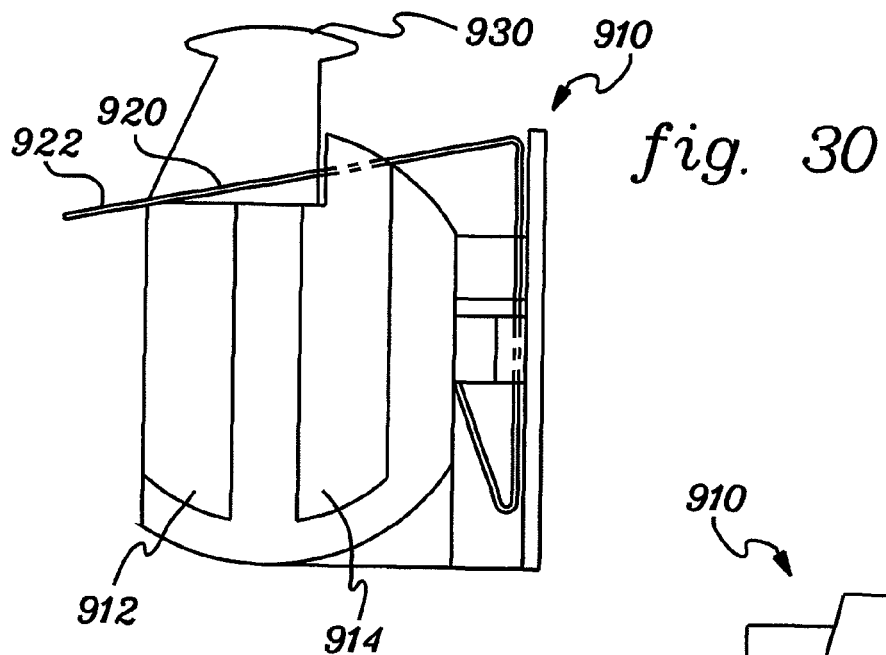
FIG. 30 is an enlarged bottom view of the plunger of FIG. 29.
Figure 31:
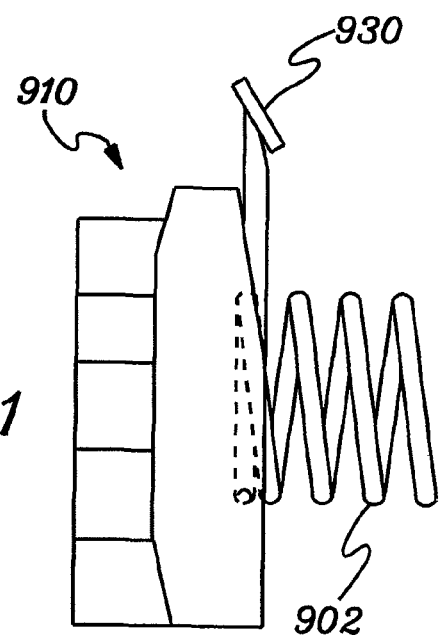
FIG. 31 is an enlarged right side elevational view of the plunger and the spring of FIG. 29.
Figure 32:
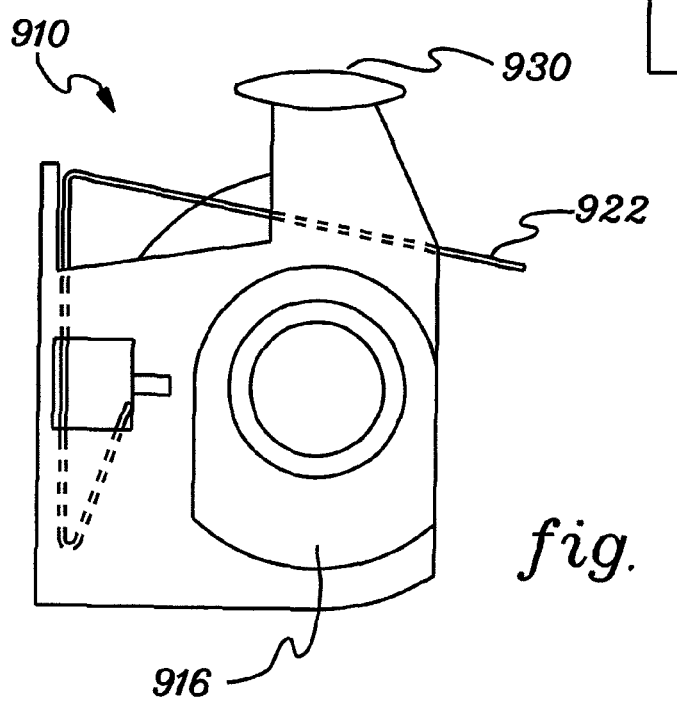
FIG. 32 is an enlarged top view of the plunger of FIG. 29.

As best shown in FIGS. 30-32, the distal end of plunger 910 includes a pair of recessed portions 912 and 914 (FIG. 30) for receiving proximal end 716 of shield 710 (FIG. 29). A proximal end of plunger 910 includes a generally annular recessed portion 916 (FIG. 32) for receiving a distal end of spring 902 (FIG. 31). In addition, plunger 910 includes flat spring member 920, which as explained in greater detail below, includes a normally downwardly biased latch 922 which is used for inhibiting the safety shield from exposing the cutting blade.

Figure 33:
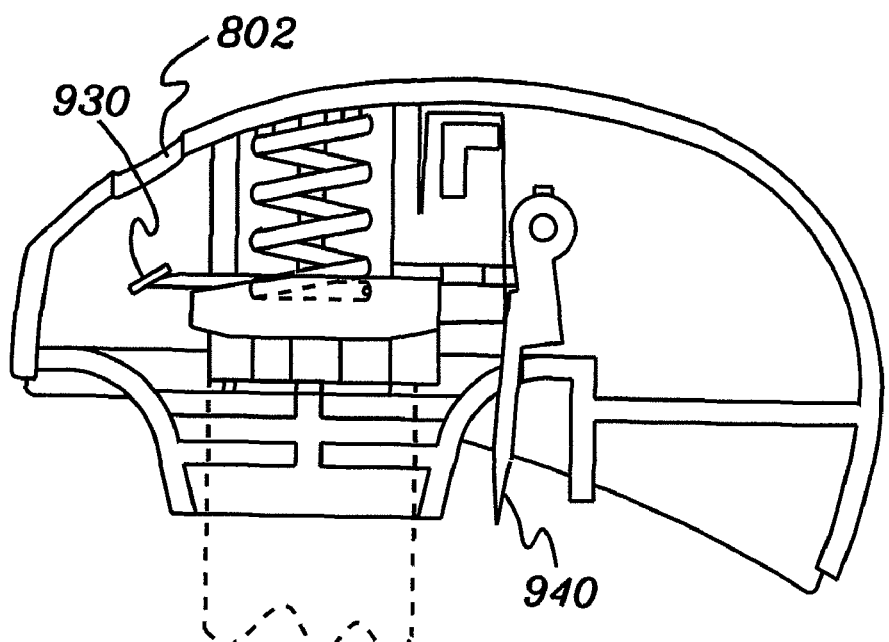
FIG. 33 is an enlarged right side elevational view of one half of the obturator cap of FIG. 29 with the locking mechanism in a locked position.
Figure 34:
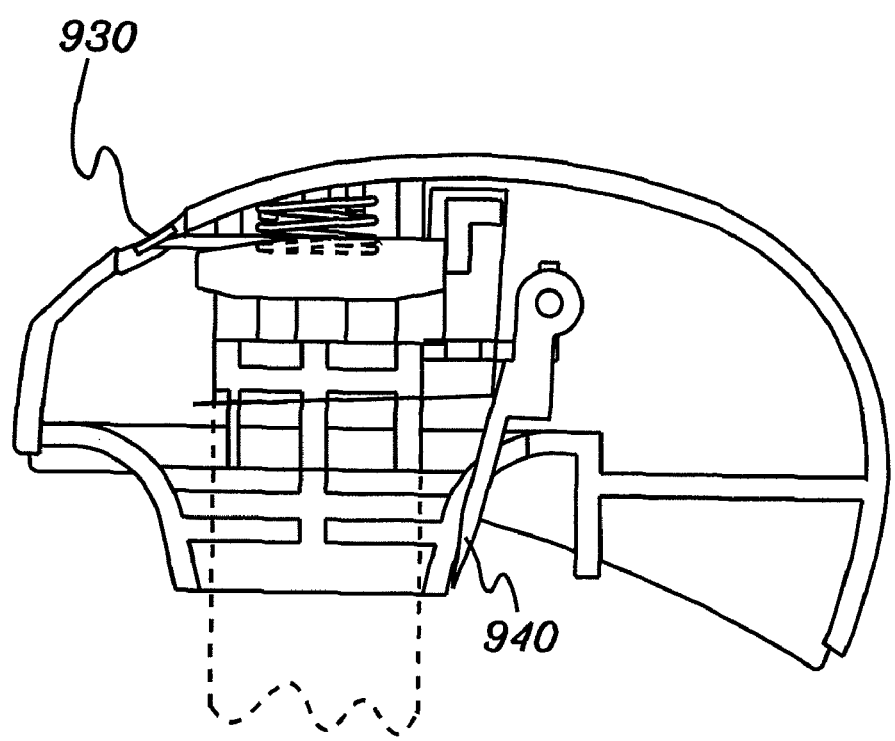
FIG. 34 is an enlarged right side elevational view of one half of the obturator cap of FIG. 29 with the locking mechanism in an unlocked position so that the shield is retractable.

Plunger 910 may also include a shield position indicator 930 which when shield 710 (FIG. 29) is permitted to move in a proximal direction, plunger 910 moves toward the proximal end of cap 800 so that indicator 930 becomes visible in an aperture 802 (FIG. 29) formed in obturator housing 800. For example, indicator 930 is normally not visible in aperture 802 as shown in FIG. 33. As shown in FIG. 34, when shield 710 (FIG. 29) is moved (e.g., when inserting the trocar system into a patient) the cutting blade is exposed, indicator 930 is disposed adjacent to aperture 802 and becomes visible to, for example, a surgeon. Plunger 910 may be formed from plastic and comprise a color such as the color red to provide a red shield position indicator or warning when viewed in the aperture formed in the obturator cap.

Figure 35:
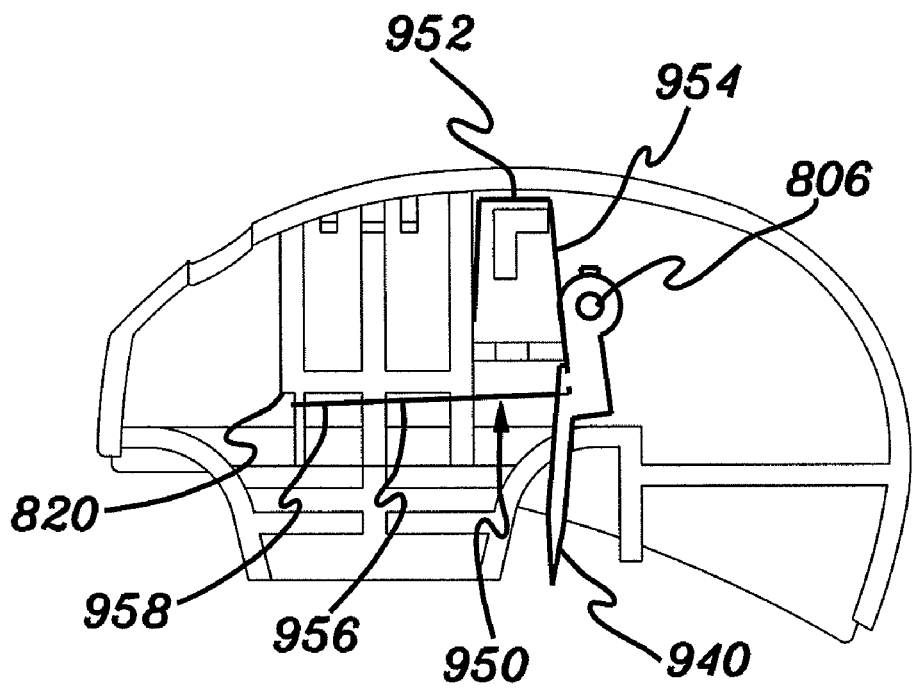
FIG. 35 is an enlarged right side elevational view of one half of the obturator cap of FIG. 29 with the actuator lever in a locked position.
Figure 36:
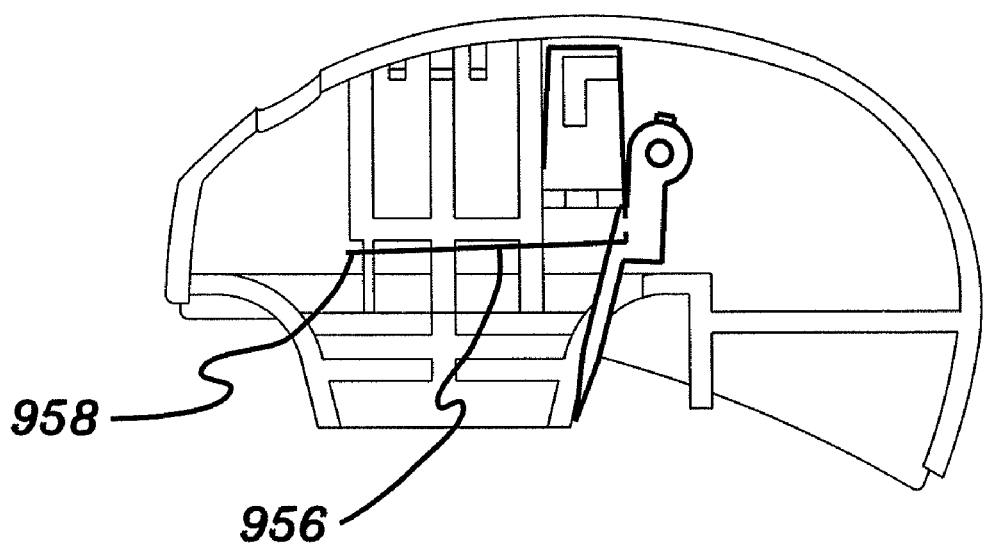
FIG. 36 is an enlarged right side elevational view of one half of the obturator cap of FIG. 29 with the actuator lever in an unlocked position.

In order to allow plunger 910 to be retracted (i.e., allow the cutting blade to be exposed), lever 940 (FIGS. 29, 33-36) must first be actuated. To accomplish this, the shielded obturator and the cannula must first be fitted together. For example, with reference to FIG. 35, lever 940 is pivotally supported on a post 806 of housing half 802 and is normally biased outwardly by generally U-shaped spring member 950. A first leg 952 is attached to housing 802, a middle portion 954 normally biases a portion of lever 940 outwardly. When lever 940 is deflected (e.g., by the releasably attachable upper seal of the cannula, a second leg 956 also moves in the direction of arrow D as shown in FIG. 36. An end 958 of second leg 956 is used to unlock plunger 910 when obturator 700 and cannula 500 are interfitted as explained in greater detail below.

Figure 37:
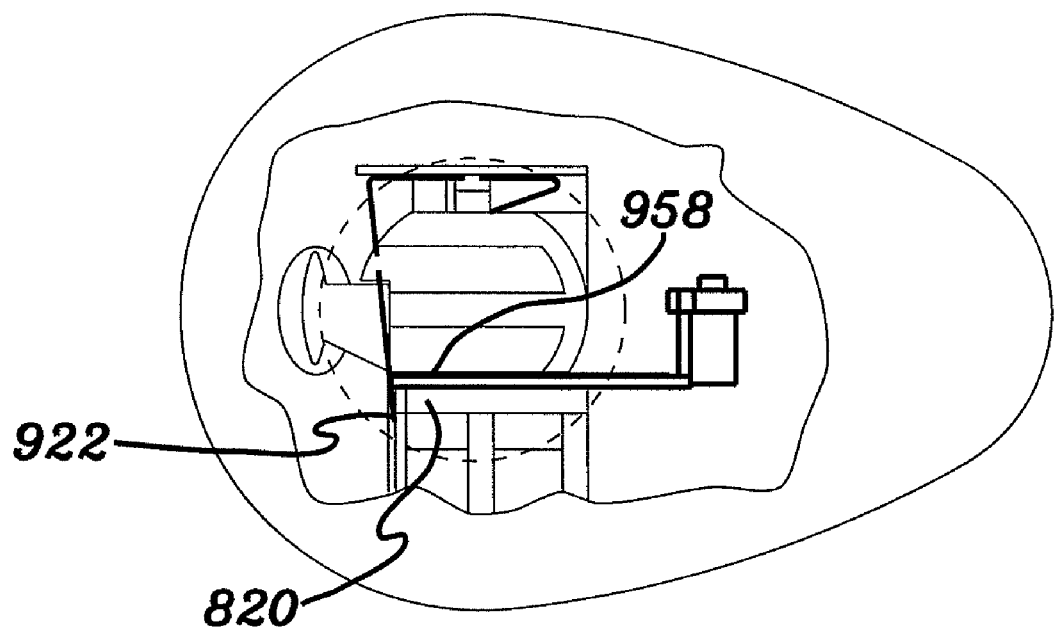
FIG. 37 is an enlarged bottom view, partially cutaway, of the obturator cap of FIG. 29 with the plunger in a locked position.
Figure 38:
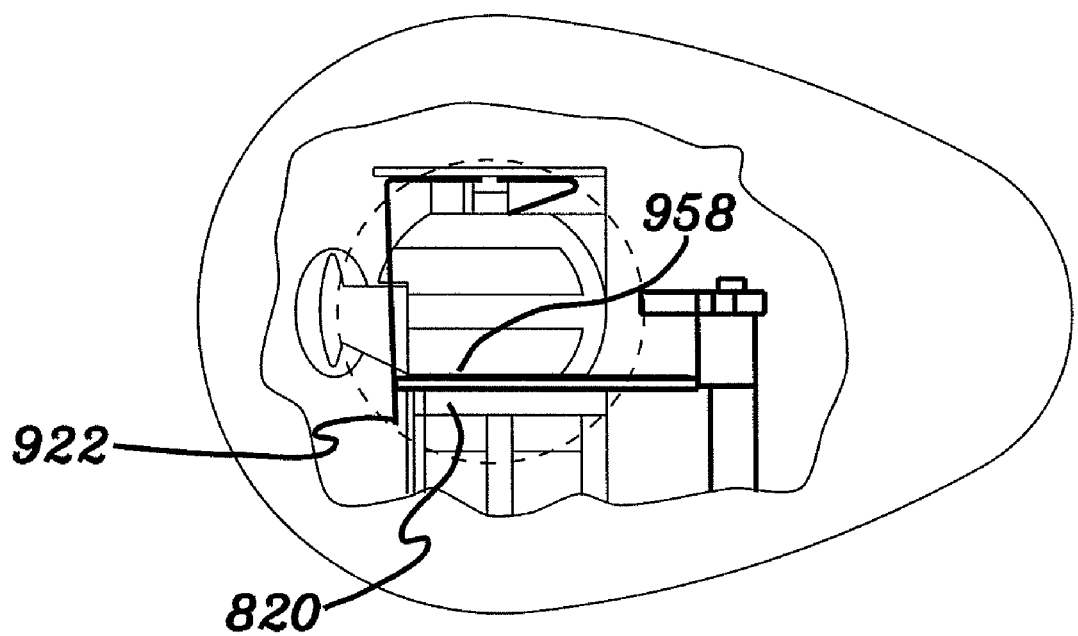
FIG. 38 is an enlarged bottom view, partially cutaway, of the obturator cap of FIG. 29 with the plunger in an unlocked position.

As shown in FIG. 37, when obturator cap and cannula head are not fitted together, end 958 of U-shaped spring 950 is positioned along side the top of a wall 820 and latch 922 is positioned on top of end 958 and against wall 820. As obturator cap and cannula head are fitted together, lever 940 moves second leg 956, as shown in FIG. 38. End 958 of second leg 956 pushes latch 922 of plunger 910 away from wall 820. Upon pressure being applied to shield 710, plunger 910 is allowed to move proximally. After the trocar system is inserted into a cavity in a patient, the shield will return to its normally biased position with latch 922 sandwiched between end 958 and wall 820. The cannula and obturator then need to be separated in order to reactivate and unlock shield 710 if further cutting is to be performed.

In another aspect of the invention, the trocar assemblies according to the present invention may include a broad range of sizes of cannulas and obturators. The cannula tubes may be typically sized to accommodate standard surgical instruments, e.g., having an outside diameters ranging from about 3 mm (0.118 inches) to about 15 mm (0.591 inches). For example, the inside diameter of cannula tube may typically range from about 3 mm (0.118 inches) to about 15 mm (0.591 inches), and preferably sized at about 5 mm (0.197 inches) and at about 12 mm (0.472 inches). The maximum diameter of obturator tube may be typically at least about 0.001 inches (0.025 mm) to about 0.020 inches (0.51 mm) greater than the inside diameter of the cannula tube, and preferably between about 0.004 inches (0.102 mm) to about 0.007 inches (0.178 mm) greater than diameter.

Figure 39:
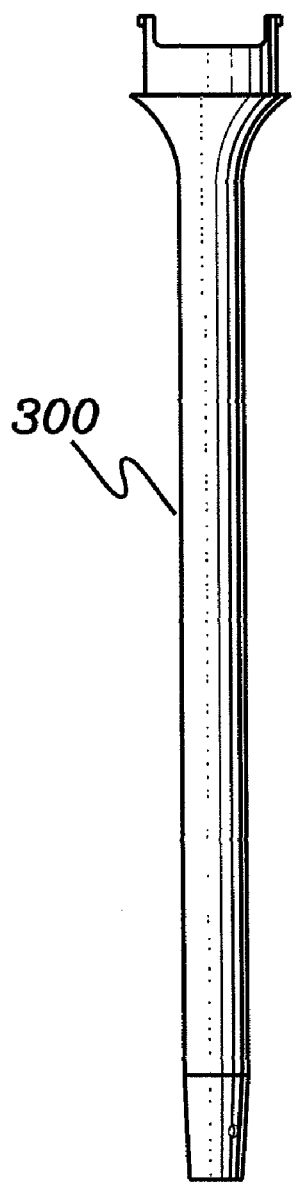
FIG. 39 is a side elevational view of the cannula tube of FIG. 1.
Figure 40:
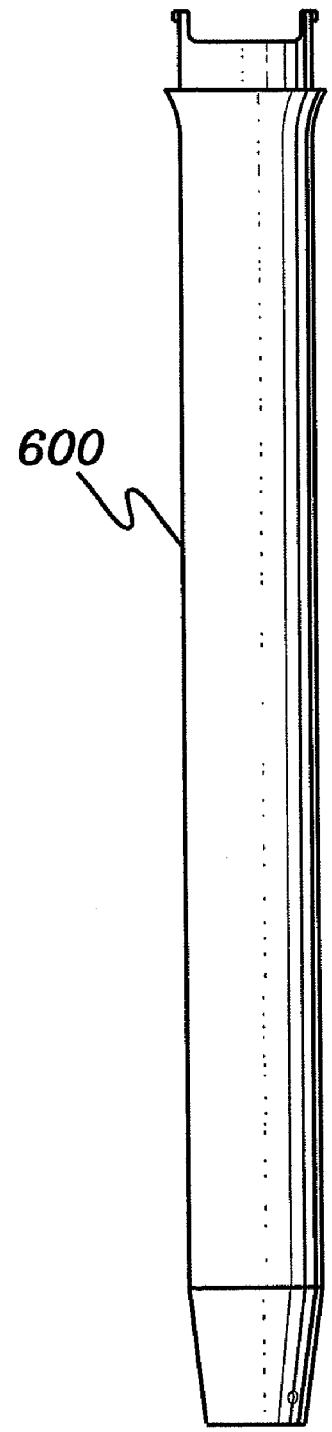
FIG. 40 is a side elevational view of the cannula tube of FIG. 2.

With reference to FIGS. 39 and 40, cannula tubes 300 and 600, respectively, may be releasably attachable to a cannula head via a bayonet style connector. In addition, the resilient non-slip material disposed around the distal opening of the cannula head may aid in forming a seal between the cannula head and the cannula tube.

In another aspect of the present invention, the cannula heads, the second releasably attachable seal, and the two halves of the obturator caps of the present invention may be interchangeable and useable to form either the cannulas and obturators shown in FIGS. 1 and 2.

Figure 41:
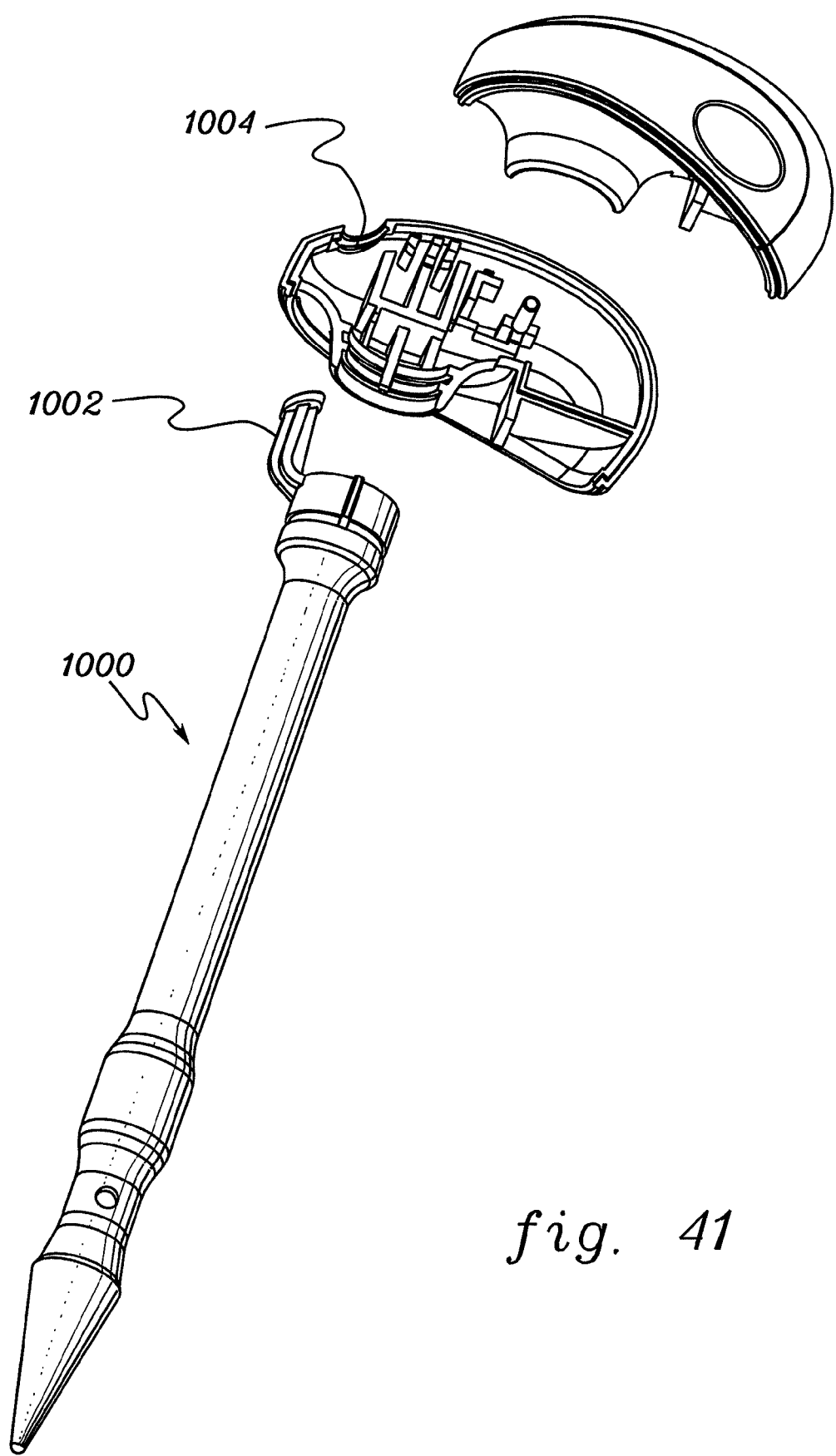
FIG. 41 is an exploded perspective view of dilating obturator in accordance with the present invention.

As shown in FIG. 41, an obturator 1000 may include an elongated shaft (having a greater shaft diameter than obturator 400). Obturator 1000 may include an arm 1002 which has a projection which covers aperture 1004 formed to the obturator cap halves.

While the invention has been particularly shown and described with reference to preferred embodiment, it will be understood by those skilled in the art that various changes in form and details may be made to the invention without departing from the spirit and scope of the invention described in the following claims.

The invention claimed is:

1. A cannula head for use in a trocar system having an obturator, said cannula head comprising:
a housing having a first passageway extending therethrough for receiving the obturator, said housing having a distal opening and a proximal opening to said first passageway;
a longitudinal axis extending through said distal opening and said proximal opening, said longitudinal axis being centered within said first passageway;
a port having a Luer Lock fitting, said port being connectable in fluid communication with said first passageway; and
wherein said housing and said port with said Luer lock fitting are monolithic, and
wherein said housing defines a modified oval-shaped cross-section arranged perpendicular to said longitudinal axis, said cross-section being asymmetrically disposed relative to said longitudinal axis such that a forward portion of said cross-section is larger in girth than a rear-portion of said cross-section.

2. The cannula head of claim 1 wherein said housing comprises a second passageway opening into said first passageway, and wherein said port opens onto said second passageway.

3. The cannula head of claim 2 further comprising a stopcock valve receivable in said second passageway for regulating the flow of fluid through said port.

4. The cannula head of claim 3 wherein said stopcock valve comprises a first position for allowing pressurized fluid through said port into said first passageway, a second position for inhibiting transfer of fluid between said first passageway and said port, and a third position for venting pressurized fluid from said first passageway through an opening in said housing separate from said port.

5. The cannula head of claim 1 wherein at least a portion of an outer surface of the housing comprises a resilient non-slip material.

6. The cannula head of claim 1 further comprising a releasably attachable seal connectable to said housing across said first passageway, a support of said releasably attachable upper seal and said housing comprise cooperating portions so that said support is rotatable in relation to said housing and about said longitudinal axis between a locked position in which said releasably attachable upper seal is connected to said housing, and an unlocked position in which said releasably attachable upper seal is removable from said housing.

7. The cannula head of claim 1 further comprising a releasably attachable upper seal connectable to said housing across said proximal opening, a support of said releasably attachable upper seal and said housing comprise cooperating portions so that said support is rotatable in relation to said housing and about said longitudinal axis between a locked position in which said releasably attachable upper seal is connected to said housing, and an unlocked position in which said releasably attachable upper seal is removable from said housing.

8. The cannula head of claim 1 wherein an area of said cross-section increases from said distal opening to said proximal opening.

9. A trocar system comprising:
a cannula head of claim 1 and a cannula tube; and
an obturator receivable in said cannula head and cannula tube.

10. The cannula of claim 1 further comprising a reusable and releasably attachable cannula tube defining a passageway extending therethrough, and wherein said cannula head and said releasably attachable cannula tube are connectable with a bayonet connector.

11. The cannula of claim 10 wherein said housing comprises a resilient material for forming a seal between said housing and said cannula tube.

12. A cannula head assembly for use in a trocar system having an obturator, said cannula head comprising:
a housing having a passageway extending therethrough defining a distal opening and a proximal opening for receiving the obturator;
a longitudinal axis extending through said distal opening and said proximal opening, said longitudinal axis being centered within said passageway; and
a releasably attachable upper seal comprising a support, a flexible seal disposed within said support, and an arm outwardly extending from said support; and
wherein said housing defines a modified oval-shaped cross-section arranged perpendicular to said longitudinal axis, said cross section being asymmetrically disposed relative to said longitudinal axis such that a forward portion of said cross section is larger in girth than a rear portion of said cross-section, and
wherein said support of said releasably attachable upper seal and said housing comprise cooperating portions so that said support is rotatable in relation to said housing and about said longitudinal axis between a locked position in which said releasably attachable upper seal is connected to said housing, and an unlocked position in which said releasably attachable upper seal is removable from said housing.

13. The cannula head of claim 12 wherein said arm extends radially away from said upper seal and a remainder of said support when viewed on a plane parallel to said cross section, the arm further comprising a knob extending proximally.

14. The cannula head of claim 12 wherein said support, said flexible seal, and said arm are disposed within said housing when said releasable attachable seal is connected to said housing.

15. The cannula head of claim 12 wherein said housing comprises indicia for indicating said locked position and said unlocked position.

16. The cannula head of claim 12 wherein said releasably attachable seal and said housing are connectable via a bayonet connector.

17. The cannula head of claim 12 further comprising a flapper valve disposed across said passageway within said housing between said support of said housing.

18. The cannula head of claim 12 wherein said flexible seal comprises a resilient member having an aperture through which the obturator is receivable.

19. The cannula head of claim 18 wherein said releasably attachable seal comprises a guard having a plurality of slits for protecting said flexible seal.

20. The cannula head of claim 12 wherein an outer surface of said housing comprises a resilient non-slip material.

21. The cannula head of claim 12 wherein an area of said cross-section increases from said distal opening to said proximal opening.

22. A trocar system comprising:
a cannula head of claim 12 and a cannula tube; and
an obturator receivable in said cannula head and cannula tube.

23. The trocar system of claim 12 wherein said cannula comprises a passageway extending along and centered about said longitudinal axis.

24. The cannula of claim 12 further comprising a reusable and releasably attachable cannula tube defining a passageway extending therethrough, and wherein said cannula head and said releasably attachable cannula tube are connectable with a bayonet connector.

25. The cannula of claim 24 wherein said housing comprises a resilient material for forming a seal between said housing and said cannula tube.

* * * * *